United States Patent
Kennedy

(10) Patent No.: US 10,813,957 B2
(45) Date of Patent: Oct. 27, 2020

(54) ENGINEERED ONCOLYTIC VIRUSES CONTAINING HYPER-BINDING SITES TO SEQUESTER AND SUPPRESS ACTIVITY OF ONCOGENIC TRANSCRIPTION FACTORS AS A NOVEL TREATMENT FOR HUMAN CANCER

(71) Applicant: Michael A. Kennedy, Oxford, OH (US)

(72) Inventor: Michael A. Kennedy, Oxford, OH (US)

(73) Assignee: Miami University, Oxford, OH (US)

( * ) Notice: Subject to any disclaimer, the term of this patent is extended or adjusted under 35 U.S.C. 154(b) by 0 days.

(21) Appl. No.: 15/288,089

(22) Filed: Oct. 7, 2016

(65) Prior Publication Data

US 2018/0099014 A1   Apr. 12, 2018

(51) Int. Cl.
| | | |
|---|---|---|
| A61K 35/761 | (2015.01) | |
| A61K 31/713 | (2006.01) | |
| C12N 15/861 | (2006.01) | |
| C12N 15/113 | (2010.01) | |
| C12N 15/115 | (2010.01) | |
| C12N 7/01 | (2006.01) | |
| C12N 7/00 | (2006.01) | |

(52) U.S. Cl.
CPC .............. *A61K 35/761* (2013.01); *C12N 7/00* (2013.01); *C12N 2710/10332* (2013.01); *Y02A 50/465* (2018.01)

(58) Field of Classification Search
None
See application file for complete search history.

(56) References Cited

U.S. PATENT DOCUMENTS

| 2009/0099108 A1* | 4/2009 | Jones | C12N 15/113 |
| | | | 514/44 R |
| 2010/0310554 A1* | 12/2010 | Holm | C12N 7/00 |
| | | | 424/133.1 |
| 2014/0107188 A1* | 4/2014 | Kennedy | A61K 9/16 |
| | | | 514/44 R |

OTHER PUBLICATIONS

Ferguson et al, Systemic Delivery of Oncolytic Viruses: Hopes and Hurdles, Advances in Virology, 2011, pp. 1-14.*
Fumoto et al, Targeted Gene Delivery, Importance of Administration Routes, Chapter 1, 2013, pp. 3-31.*
Green and Seymour, Review: Adenoviral vectors: Systemic delivery and tumor targeting, 2002, pp. 1036-1042.*
Cherubini et al, The oncolytic adenovirus AdDD enhances selective cancer cell killing in combination with DNA-damaging drugs in pancreatic cancer models, Gene Therapy, 2011, pp. 1157-1165.*
Cohen et al, How viruses access the nucleus, Biochimica et Biophysica Acta 1813 (2011) 1634-1645.*

* cited by examiner

*Primary Examiner* — Maria Marvich
(74) *Attorney, Agent, or Firm* — Renner Kenner Greive Bobak Taylor & Weber

(57) ABSTRACT

In one or more embodiments, the present invention provides novel artificial, non-naturally-occurring double stranded DNA segments (and related methods) capable of acting as decoy binding sites for oncogenic transcription factors and a general method for suppressing aberrant activity of oncogenic transcription factors that promote cancer progression. In various embodiments, the present invention involves the sequestration of targeted oncogenic transcription factors at these artificial, non-naturally occurring engineered transcription factor binding sites, which have been introduced into the cells using oncolytic or other viruses that can be engineered to selectively target cancer cells. These artificial, non-naturally occurring engineered transcription factor binding sites act as decoys for binding so as to competitively sequester oncogenic transcription factors away from the host genomic DNA, thus abolishing or reducing oncogenic transcription factor activity and resulting in restored sensitivity to chemotherapy, increased apoptosis, and reduced cancer cell proliferation.

14 Claims, 9 Drawing Sheets

Specification includes a Sequence Listing.

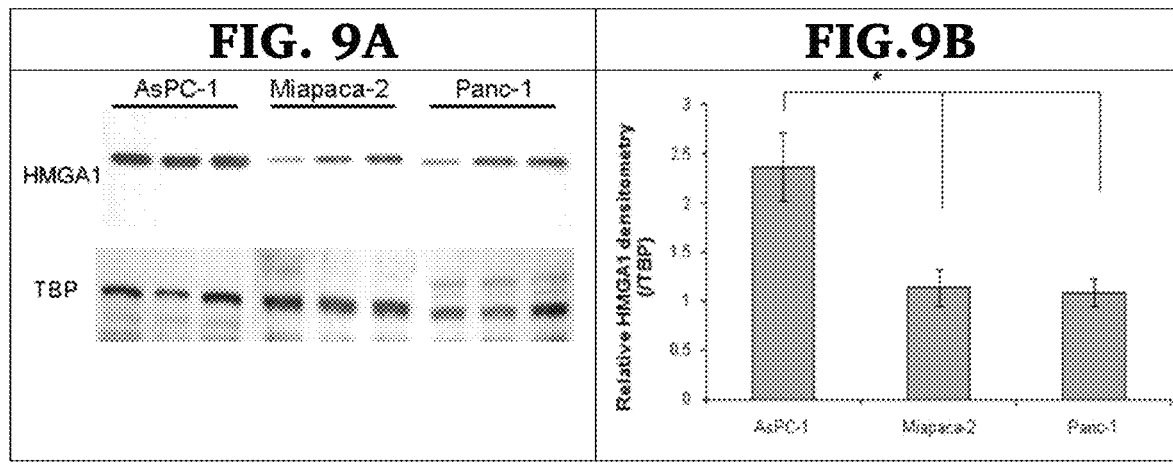
FIG. 9A
FIG. 9B
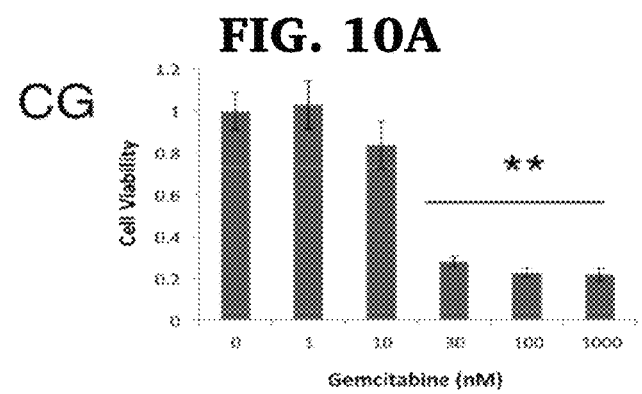
FIG. 10A
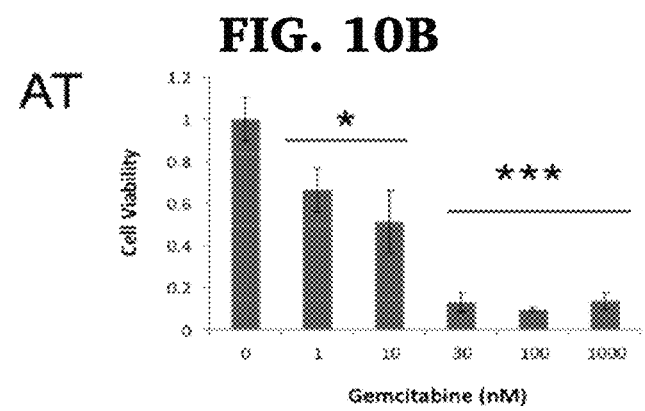
FIG. 10B

FIG. 11A  FIG. 11B  FIG. 11C
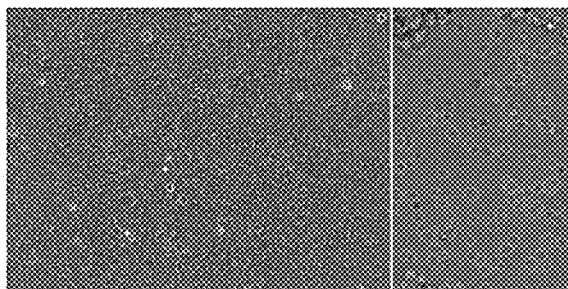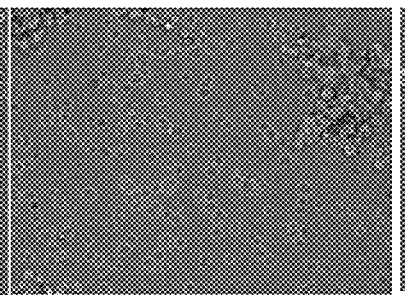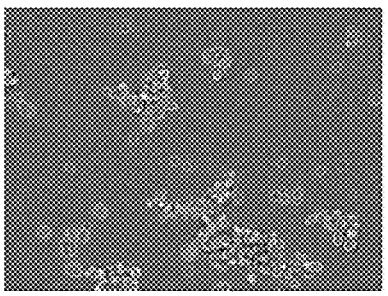
FIG. 12A  FIG. 12B
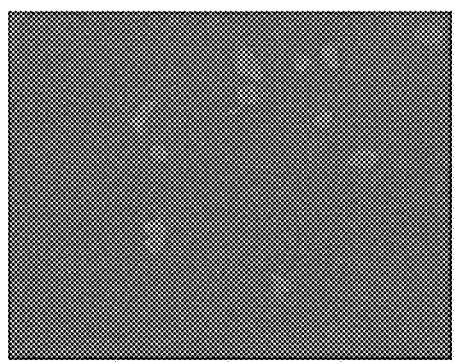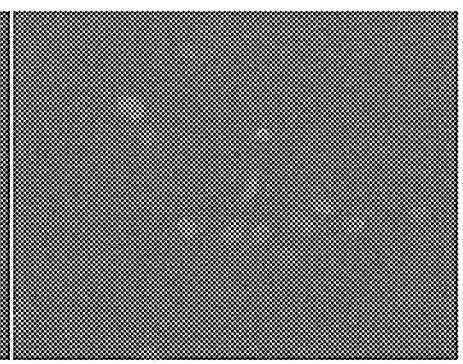
FIG. 13A  FIG. 13B  FIG. 13C
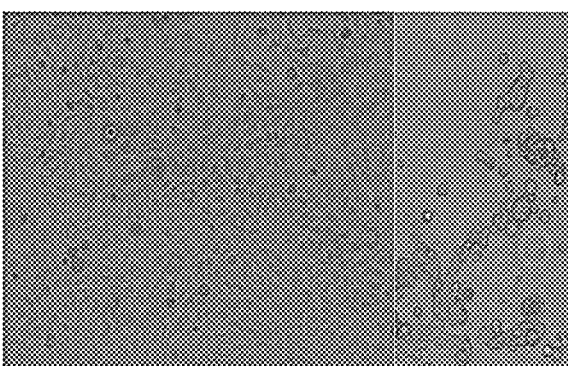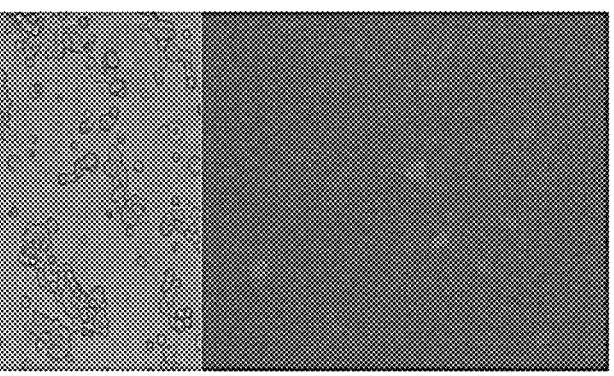

SEQUENCE LISTING

```
<160> NUMBER OF SEQ ID NOS: 16

<210> SEQ ID NO 1
<211> LENGTH: 170
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (131)..(170)
<223> OTHER INFORMATION: n is any nucleotide and up to 40 nucleotides
      may be absent.

<400> SEQUENCE: 1
nnnnnnnnnn nnnnnnnnnn nnnnnnnnnn nnnnnnnnnn aaaaaaaaaa aaaaattttt      60 ttttttttt aaaaaaaaaa aaaaaaaaaa aaaaaaaaaa aaaaaaaaaa aaaaattttt     120
tttttttttt nnnnnnnnnn nnnnnnnnnn nnnnnnnnnn nnnnnnnnnn               170

<210> SEQ ID NO 2
<211> LENGTH: 170
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (41)..(130)
<223> OTHER INFORMATION: w is a thymine (t) or adenine (a) nucleotide.
<220> FEATURE:
<221> NAME/KEY: misc_feature
<222> LOCATION: (131)..(170)
```

```
<223>  OTHER INFORMATION: n is any nucleotide and up to 40 nucleotides
       may be absent.

<400>  SEQUENCE: 2 nnnnnnnnnn nnnnnnnnnn nnnnnnnnnn nnnnnnnnnn wwwwwwwwww wwwwwwwwww      60
wwwwwwwwww wwwwwwwwww wwwwwwwwww wwwwwwwwww wwwwwwwwww wwwwwwwwww     120
wwwwwwwwww nnnnnnnnnn nnnnnnnnnn nnnnnnnnnn nnnnnnnnnn                170

<210>  SEQ ID NO 3
<211>  LENGTH: 370
<212>  TYPE: DNA
<213>  ORGANISM: Artificial
<220>  FEATURE:
<223>  OTHER INFORMATION: Synthetic DNA sequence
<220>  FEATURE:
<221>  NAME/KEY: misc_feature
<222>  LOCATION: (1)..(40)
<223>  OTHER INFORMATION: n is any nucleotide and up to 40 nucleotides
       may be absent.
<220>  FEATURE:
<221>  NAME/KEY: misc_feature
<222>  LOCATION: (56)..(95)
<223>  OTHER INFORMATION: n is any nucleotide and up to 40 nucleotides
       may be absent.
<220>  FEATURE:
<221>  NAME/KEY: misc_feature
<222>  LOCATION: (111)..(150)
<223>  OTHER INFORMATION: n is any nucleotide and up to 40 nucleotides
       may be absent.
<220>  FEATURE:
<221>  NAME/KEY: misc_feature
<222>  LOCATION: (166)..(205)
<223>  OTHER INFORMATION: n is any nucleotide and up to 40 nucleotides
       may be absent.
<220>  FEATURE:
<221>  NAME/KEY: misc_feature
<222>  LOCATION: (221)..(260)
<223>  OTHER INFORMATION: n is any nucleotide and up to 40 nucleotides
       may be absent.
<220>  FEATURE:
<221>  NAME/KEY: misc_feature
<222>  LOCATION: (276)..(315)
<223>  OTHER INFORMATION: n is any nucleotide and up to 40 nucleotides
       may be absent.
<220>  FEATURE:
<221>  NAME/KEY: misc_feature
<222>  LOCATION: (331)..(370)
<223>  OTHER INFORMATION: n is any nucleotide and up to 40 nucleotides
       may be absent.

<400>  SEQUENCE: 3 nnnnnnnnnn nnnnnnnnnn nnnnnnnnnn nnnnnnnnnn aaaaaaaaaa aaaaannnnn      60
nnnnnnnnnn nnnnnnnnnn nnnnnnnnnn nnnnntttt ttttttttt nnnnnnnnnn     120 nnnnnnnnnn nnnnnnnnnn nnnnnnnnnn aaaaaaaaaa aaaaannnnn nnnnnnnnnn     180
nnnnnnnnnn nnnnnnnnnn nnnnnaaaaa aaaaaaaaaa nnnnnnnnnn nnnnnnnnnn     240
nnnnnnnnnn nnnnnnnnnn aaaaaaaaaa aaaaannnnn nnnnnnnnnn nnnnnnnnnn     300
nnnnnnnnnn nnnnntttt ttttttttt nnnnnnnnnn nnnnnnnnnn nnnnnnnnnn     360 nnnnnnnnnn                                                              370

<210>  SEQ ID NO 4
<211>  LENGTH: 370
<212>  TYPE: DNA
<213>  ORGANISM: Artificial
<220>  FEATURE:
<223>  OTHER INFORMATION: Synthetic DNA sequence
<220>  FEATURE:
<221>  NAME/KEY: misc_feature
```

<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (41)..(55)
<223> OTHER INFORMATION: w is a thymine (t) or adenine (a) nucleotide
<220> FEATURE:
<221> NAME/KEY: misc_feature
<222> LOCATION: (56)..(95)
<223> OTHER INFORMATION: n is any nucleotide and up to 40 nucleotides
      may be absent.
<220> FEATURE:
<221> NAME/KEY: misc_feature
<222> LOCATION: (96)..(110)
<223> OTHER INFORMATION: w is a thymine (t) or adenine (a) nucleotide
<220> FEATURE:
<221> NAME/KEY: misc_feature
<222> LOCATION: (111)..(150)
<223> OTHER INFORMATION: w is a thymine (t) or adenine (a) nucleotide
<220> FEATURE:
<221> NAME/KEY: misc_feature
<222> LOCATION: (151)..(165)
<223> OTHER INFORMATION: w is a thymine (t) or adenine (a) nucleotide
<220> FEATURE:
<221> NAME/KEY: misc_feature
<222> LOCATION: (166)..(205)
<223> OTHER INFORMATION: n is any nucleotide and up to 40 nucleotides
      may be absent.
<220> FEATURE:
<221> NAME/KEY: misc_feature
<222> LOCATION: (206)..(220)
<223> OTHER INFORMATION: w is a thymine (t) or adenine (a) nucleotide
<220> FEATURE:
<221> NAME/KEY: misc_feature
<222> LOCATION: (221)..(260)
<223> OTHER INFORMATION: n is any nucleotide and up to 40 nucleotides
      may be absent.
<220> FEATURE:
<221> NAME/KEY: misc_feature
<222> LOCATION: (261)..(275)
<223> OTHER INFORMATION: w is a thymine (t) or adenine (a) nucleotide
<220> FEATURE:
<221> NAME/KEY: misc_feature
<222> LOCATION: (276)..(315)
<223> OTHER INFORMATION: w is a thymine (t) or adenine (a) nucleotide
<220> FEATURE:
<221> NAME/KEY: misc_feature
<222> LOCATION: (316)..(330)
<223> OTHER INFORMATION: w is a thymine (t) or adenine (a) nucleotide
<220> FEATURE:
<221> NAME/KEY: misc_feature
<222> LOCATION: (331)..(370)
<223> OTHER INFORMATION: n is any nucleotide and up to 40 nucleotides
      may be absent.

<400> SEQUENCE: 4
nnnnnnnnnn nnnnnnnnnn nnnnnnnnnn nnnnnnnnnn wwwwwwwww wwwwnnnnn            60 nnnnnnnnnn nnnnnnnnnn nnnnnnnnnn nnnnwwwww wwwwwwwww nnnnnnnnnn            120 nnnnnnnnnn nnnnnnnnnn nnnnnnnnnn wwwwwwwww wwwwnnnnn nnnnnnnnnn            180 nnnnnnnnnn nnnnnnnnnn nnnnwwwww wwwwwwwww nnnnnnnnnn nnnnnnnnnn            240
nnnnnnnnnn nnnnnnnnnn wwwwwwwww wwwwnnnnn nnnnnnnnnn nnnnnnnnnn            300
nnnnnnnnnn nnnnwwwww wwwwwwwww nnnnnnnnnn nnnnnnnnnn nnnnnnnnnn            360 nnnnnnnnnn                                                                  370

<210> SEQ ID NO 5
<211> LENGTH: 140
<212> TYPE: DNA
<213> ORGANISM: Artificial
<220> FEATURE:
<223> OTHER INFORMATION: Synthetic DNA sequence

```
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (101)..(140)
<223> OTHER INFORMATION: n is any nucleotide and up to 40 nucleotides
      may be absent.

<400> SEQUENCE: 5
nnnnnnnnnn nnnnnnnnnn nnnnnnnnnn nnnnnnnnnn agaacaatgg agaacaatgg      60
agaacaatgg agaacaatgg agaacaatgg agaacaatgg nnnnnnnnnn nnnnnnnnnn     120
nnnnnnnnnn nnnnnnnnnn                                                 140

<210> SEQ ID NO 6
<211> LENGTH: 340
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (51)..(90)
<223> OTHER INFORMATION: n is any nucleotide and up to 40 nucleotides
      may be absent.
<220> FEATURE:
<221> NAME/KEY: misc_feature
<222> LOCATION: (101)..(140)
<223> OTHER INFORMATION: n is any nucleotide and up to 40 nucleotides
      may be absent.
<220> FEATURE:
<221> NAME/KEY: misc_feature
<222> LOCATION: (151)..(190)
<223> OTHER INFORMATION: n is any nucleotide and up to 40 nucleotides
      may be absent.
<220> FEATURE:
<221> NAME/KEY: misc_feature
<222> LOCATION: (201)..(240)
<223> OTHER INFORMATION: n is any nucleotide and up to 40 nucleotides
      may be absent.
<220> FEATURE:
<221> NAME/KEY: misc_feature
<222> LOCATION: (251)..(290)
<223> OTHER INFORMATION: n is any nucleotide and up to 40 nucleotides
      may be absent.
<220> FEATURE:
<221> NAME/KEY: misc_feature
<222> LOCATION: (301)..(340)
<223> OTHER INFORMATION: n is any nucleotide and up to 40 nucleotides
      may be absent.

<400> SEQUENCE: 6
nnnnnnnnnn nnnnnnnnnn nnnnnnnnnn nnnnnnnnnn agaacaatgg nnnnnnnnnn      60
nnnnnnnnnn nnnnnnnnnn nnnnnnnnnn agaacaatgg nnnnnnnnnn nnnnnnnnnn     120
nnnnnnnnnn nnnnnnnnnn agaacaatgg nnnnnnnnnn nnnnnnnnnn nnnnnnnnnn     180
nnnnnnnnnn agaacaatgg nnnnnnnnnn nnnnnnnnnn nnnnnnnnnn nnnnnnnnnn     240
agaacaatgg nnnnnnnnnn nnnnnnnnnn nnnnnnnnnn nnnnnnnnnn agaacaatgg     300
nnnnnnnnnn nnnnnnnnnn nnnnnnnnnn nnnnnnnnnn                           340

<210> SEQ ID NO 7
<211> LENGTH: 122
```

```
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (83)..(122)
<223> OTHER INFORMATION: n is any nucleotide and up to 40 nucleotides
      may be absent.

<400> SEQUENCE: 7
nnnnnnnnnn nnnnnnnnnn nnnnnnnnnn nnnnnnnnnn tgactcatga ctcatgactc      60
atgactcatg actcatgact cannnnnnnn nnnnnnnnnn nnnnnnnnnn nnnnnnnnnn     120 nn                                                                    122

<210> SEQ ID NO 8
<211> LENGTH: 322
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (48)..(87)
<223> OTHER INFORMATION: n is any nucleotide and up to 40 nucleotides
      may be absent.
<220> FEATURE:
<221> NAME/KEY: misc_feature
<222> LOCATION: (95)..(134)
<223> OTHER INFORMATION: n is any nucleotide and up to 40 nucleotides
      may be absent.
<220> FEATURE:
<221> NAME/KEY: misc_feature
<222> LOCATION: (142)..(181)
<223> OTHER INFORMATION: n is any nucleotide and up to 40 nucleotides
      may be absent.
<220> FEATURE:
<221> NAME/KEY: misc_feature
<222> LOCATION: (189)..(228)
<223> OTHER INFORMATION: n is any nucleotide and up to 40 nucleotides
      may be absent.
<220> FEATURE:
<221> NAME/KEY: misc_feature
<222> LOCATION: (236)..(275)
<223> OTHER INFORMATION: n is any nucleotide and up to 40 nucleotides
      may be absent.
<220> FEATURE:
<221> NAME/KEY: misc_feature
<222> LOCATION: (283)..(322)
<223> OTHER INFORMATION: n is any nucleotide and up to 40 nucleotides
      may be absent.

<400> SEQUENCE: 8
nnnnnnnnnn nnnnnnnnnn nnnnnnnnnn nnnnnnnnnn tgactcannn nnnnnnnnnn      60
nnnnnnnnnn nnnnnnnnnn nnnnnnntga ctcannnnnn nnnnnnnnnn nnnnnnnnnn     120
nnnnnnnnnn nnnntgactc annnnnnnnn nnnnnnnnnn nnnnnnnnnn nnnnnnnnnn     180
ntgactcann nnnnnnnnnn nnnnnnnnnn nnnnnnnnnn nnnnnnnntg actcannnnn     240
nnnnnnnnnn nnnnnnnnnn nnnnnnnnnn nnnntgactc annnnnnnnn nnnnnnnnnn     300
nnnnnnnnnn nnnnnnnnnn nn                                              322
```

<210> SEQ ID NO 9
<211> LENGTH: 128
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (43)..(46)
<223> OTHER INFORMATION: n is a, c, g, or t
<220> FEATURE:
<221> NAME/KEY: misc_feature
<222> LOCATION: (51)..(54)
<223> OTHER INFORMATION: n is a, c, g, or t
<220> FEATURE:
<221> NAME/KEY: misc_feature
<222> LOCATION: (59)..(62)
<223> OTHER INFORMATION: n is a, c, g, or t
<220> FEATURE:
<221> NAME/KEY: misc_feature
<222> LOCATION: (67)..(70)
<223> OTHER INFORMATION: n is a, c, g, or t
<220> FEATURE:
<221> NAME/KEY: misc_feature
<222> LOCATION: (75)..(78)
<223> OTHER INFORMATION: n is a, c, g, or t
<220> FEATURE:
<221> NAME/KEY: misc_feature
<222> LOCATION: (83)..(86)
<223> OTHER INFORMATION: n is a, c, g, or t
<220> FEATURE:
<221> NAME/KEY: misc_feature
<222> LOCATION: (89)..(128)
<223> OTHER INFORMATION: n is any nucleotide and up to 40 nucleotides
      may be absent.

<400> SEQUENCE: 9 nnnnnnnnn nnnnnnnnn nnnnnnnnn nnnnnnnnn ttnnnnaatt nnnnaattnn        60
nnaattnnnn aattnnnnaa ttnnnnaann nnnnnnnnn nnnnnnnnn nnnnnnnnn       120 nnnnnnnn                                                            128

<210> SEQ ID NO 10
<211> LENGTH: 328
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (43)..(46)
<223> OTHER INFORMATION: n is any nucleotide.
<220> FEATURE:
<221> NAME/KEY: misc_feature
<222> LOCATION: (49)..(88)
<223> OTHER INFORMATION: n is any nucleotide and up to 40 nucleotides
      may be absent.
<220> FEATURE:
<221> NAME/KEY: misc_feature
<222> LOCATION: (91)..(94)
<223> OTHER INFORMATION: n is any nucleotide.
<220> FEATURE:
<221> NAME/KEY: misc_feature
<222> LOCATION: (97)..(136)

```
<223> OTHER INFORMATION: n is any nucleotide and up to 40 nucleotides
      may be absent.
<220> FEATURE:
<221> NAME/KEY: misc_feature
<222> LOCATION: (139)..(142)
<223> OTHER INFORMATION: n is any nucleotide.
<220> FEATURE:
<221> NAME/KEY: misc_feature
<222> LOCATION: (145)..(184)
<223> OTHER INFORMATION: n is any nucleotide and up to 40 nucleotides
      may be absent.
<220> FEATURE:
<221> NAME/KEY: misc_feature
<222> LOCATION: (187)..(190)
<223> OTHER INFORMATION: n is any nucleotide.
<220> FEATURE:
<221> NAME/KEY: misc_feature
<222> LOCATION: (193)..(232)
<223> OTHER INFORMATION: n is any nucleotide and up to 40 nucleotides
      may be absent.
<220> FEATURE:
<221> NAME/KEY: misc_feature
<222> LOCATION: (235)..(238)
<223> OTHER INFORMATION: n is any nucleotide.
<220> FEATURE:
<221> NAME/KEY: misc_feature
<222> LOCATION: (241)..(280)
<223> OTHER INFORMATION: n is any nucleotide and up to 40 nucleotides
      may be absent.
<220> FEATURE:
<221> NAME/KEY: misc_feature
<222> LOCATION: (283)..(286)
<223> OTHER INFORMATION: n is any nucleotide.
<220> FEATURE:
<221> NAME/KEY: misc_feature
<222> LOCATION: (289)..(328)
<223> OTHER INFORMATION: n is any nucleotide and up to 40 nucleotides
      may be absent.

<400> SEQUENCE: 10
nnnnnnnnnn nnnnnnnnnn nnnnnnnnnn nnnnnnnnnn ttnnnnaann nnnnnnnnnn      60
nnnnnnnnnn nnnnnnnnnn nnnnnnnntt nnnnaannnn nnnnnnnnnn nnnnnnnnnn     120
nnnnnnnnnn nnnnnnttnn nnaannnnnn nnnnnnnnnn nnnnnnnnnn nnnnnnnnnn     180
nnnnttnnnn aannnnnnnn nnnnnnnnnn nnnnnnnnnn nnnnnnnnnn nnttnnnnaa     240
nnnnnnnnnn nnnnnnnnnn nnnnnnnnnn nnnnnnnnnn ttnnnnaann nnnnnnnnnn     300
nnnnnnnnnn nnnnnnnnnn nnnnnnnn                                       328

<210> SEQ ID NO 11
<211> LENGTH: 134
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (43)..(47)
<223> OTHER INFORMATION: n is any nucleotide
<220> FEATURE:
<221> NAME/KEY: misc_feature
<222> LOCATION: (52)..(57)
<223> OTHER INFORMATION: n is any nucleotide
<220> FEATURE:
<221> NAME/KEY: misc_feature
<222> LOCATION: (61)..(65)
<223> OTHER INFORMATION: n is any nucleotide
<220> FEATURE:
<221> NAME/KEY: misc_feature
```

```
<222> LOCATION: (70)..(74)
<223> OTHER INFORMATION: n is any nucleotide
<220> FEATURE:
<221> NAME/KEY: misc_feature
<222> LOCATION: (79)..(83)
<223> OTHER INFORMATION: n is any nucleotide
<220> FEATURE:
<221> NAME/KEY: misc_feature
<222> LOCATION: (88)..(92)
<223> OTHER INFORMATION: n is any nucleotide
<220> FEATURE:
<221> NAME/KEY: misc_feature
<222> LOCATION: (95)..(134)
<223> OTHER INFORMATION: n is any nucleotide and up to 40 nucleotides
      may be absent.

<400> SEQUENCE: 11
nnnnnnnnnn nnnnnnnnnn nnnnnnnnnn nnnnnnnnnn ttnnnnnaat tnnnnnaatt      60
nnnnnaattn nnnnaattnn nnnaattnnn nnaannnnnn nnnnnnnnnn nnnnnnnnnn     120
nnnnnnnnnn nnnn                                                      134

<210> SEQ ID NO 12
<211> LENGTH: 328
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (43)..(46)
<223> OTHER INFORMATION: n is any nucleotide
<220> FEATURE:
<221> NAME/KEY: misc_feature
<222> LOCATION: (49)..(88)
<223> OTHER INFORMATION: n is any nucleotide and up to 40 nucleotides
      may be absent.
<220> FEATURE:
<221> NAME/KEY: misc_feature
<222> LOCATION: (91)..(94)
<223> OTHER INFORMATION: n is any nucleotide
<220> FEATURE:
<221> NAME/KEY: misc_feature
<222> LOCATION: (97)..(136)
<223> OTHER INFORMATION: n is any nucleotide and up to 40 nucleotides
      may be absent.
<220> FEATURE:
<221> NAME/KEY: misc_feature
<222> LOCATION: (139)..(142)
<223> OTHER INFORMATION: n is any nucleotide
<220> FEATURE:
<221> NAME/KEY: misc_feature
<222> LOCATION: (145)..(184)
<223> OTHER INFORMATION: n is any nucleotide and up to 40 nucleotides
      may be absent.
<220> FEATURE:
<221> NAME/KEY: misc_feature
<222> LOCATION: (187)..(190)
<223> OTHER INFORMATION: n is any nucleotide
<220> FEATURE:
<221> NAME/KEY: misc_feature
<222> LOCATION: (193)..(232)
<223> OTHER INFORMATION: n is any nucleotide and up to 40 nucleotides
      may be absent.
<220> FEATURE:
<221> NAME/KEY: misc_feature
<222> LOCATION: (235)..(238)
<223> OTHER INFORMATION: n is any nucleotide
<220> FEATURE:
<221> NAME/KEY: misc_feature
<222> LOCATION: (241)..(280)
```

<223> OTHER INFORMATION: n is any nucleotide and up to 40 nucleotides
      may be absent.
<220> FEATURE:
<221> NAME/KEY: misc_feature
<222> LOCATION: (283)..(286)
<223> OTHER INFORMATION: n is any nucleotide
<220> FEATURE:
<221> NAME/KEY: misc_feature
<222> LOCATION: (289)..(328)
<223> OTHER INFORMATION: n is any nucleotide and up to 40 nucleotides
      may be absent.

<400> SEQUENCE: 12
nnnnnnnnnn nnnnnnnnnn nnnnnnnnnn nnnnnnnnnn ttnnnnaann nnnnnnnnnn      60
nnnnnnnnnn nnnnnnnnnn nnnnnnnntt nnnnaannnn nnnnnnnnnn nnnnnnnnnn     120
nnnnnnnnnn nnnnnnttnn nnaannnnnn nnnnnnnnnn nnnnnnnnnn nnnnnnnnnn     180
nnnnttnnnn aannnnnnnn nnnnnnnnnn nnnnnnnnnn nnnnnnnnnn nnttnnnnaa     240
nnnnnnnnnn nnnnnnnnnn nnnnnnnnnn nnnnnnnnnn ttnnnnaann nnnnnnnnnn     300
nnnnnnnnnn nnnnnnnnnn nnnnnnnn                                        328

<210> SEQ ID NO 13
<211> LENGTH: 140
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (41)..(160)
<223> OTHER INFORMATION: n is any nucleotide; r is a purine (g or a);
      and y is a pyrimidine (t or c)
<220> FEATURE:
<221> NAME/KEY: misc_feature
<222> LOCATION: (101)..(140)
<223> OTHER INFORMATION: n is any nucleotide and up to 40 nucleotides
      may be absent.

<400> SEQUENCE: 13
nnnnnnnnnn nnnnnnnnnn nnnnnnnnnn nnnnnnnnnn gggrnyyycc gggrnyyycc      60
gggrnyyycc gggrnyyycc gggrnyyycc gggrnyyycc nnnnnnnnnn nnnnnnnnnn     120
nnnnnnnnnn nnnnnnnnnn                                                 140

<210> SEQ ID NO 14
<211> LENGTH: 340
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
<222> LOCATION: (41)..(50)
<223> OTHER INFORMATION: n is any nucleotide; r is a purine (g or a);
      and y is a pyrimidine (t or c).
<220> FEATURE:
<221> NAME/KEY: misc_feature
<222> LOCATION: (51)..(90)
<223> OTHER INFORMATION: n is any nucleotide and up to 40 nucleotides
      may be absent.

```
<220> FEATURE:
<221> NAME/KEY: misc_feature
<222> LOCATION: (91)..(100)
<223> OTHER INFORMATION: n is any nucleotide; r is a purine (g or a);
      and y is a pyrimidine (t or c).
<220> FEATURE:
<221> NAME/KEY: misc_feature
<222> LOCATION: (101)..(140)
<223> OTHER INFORMATION: n is any nucleotide and up to 40 nucleotides
      may be absent.
<220> FEATURE:
<221> NAME/KEY: misc_feature
<222> LOCATION: (141)..(150)
<223> OTHER INFORMATION: n is any nucleotide; r is a purine (g or a);
      and y is a pyrimidine (t or c).
<220> FEATURE:
<221> NAME/KEY: misc_feature
<222> LOCATION: (151)..(190)
<223> OTHER INFORMATION: n is any nucleotide; r is a purine (g or a);
      and y is a pyrimidine (t or c).
<220> FEATURE:
<221> NAME/KEY: misc_feature
<222> LOCATION: (191)..(200)
<223> OTHER INFORMATION: n is any nucleotide; r is a purine (g or a);
      and y is a pyrimidine (t or c).
<220> FEATURE:
<221> NAME/KEY: misc_feature
<222> LOCATION: (201)..(240)
<223> OTHER INFORMATION: n is any nucleotide and up to 40 nucleotides
      may be absent.
<220> FEATURE:
<221> NAME/KEY: misc_feature
<222> LOCATION: (241)..(250)
<223> OTHER INFORMATION: n is any nucleotide; r is a purine (g or a);
      and y is a pyrimidine (t or c).
<220> FEATURE:
<221> NAME/KEY: misc_feature
<222> LOCATION: (251)..(290)
<223> OTHER INFORMATION: n is any nucleotide and up to 40 nucleotides
      may be absent.
<220> FEATURE:
<221> NAME/KEY: misc_feature
<222> LOCATION: (291)..(300)
<223> OTHER INFORMATION: n is any nucleotide and up to 40 nucleotides
      may be absent.
<220> FEATURE:
<221> NAME/KEY: misc_feature
<222> LOCATION: (301)..(340)
<223> OTHER INFORMATION: n is any nucleotide and up to 40 nucleotides
      may be absent.

<400> SEQUENCE: 14
nnnnnnnnnn nnnnnnnnnn nnnnnnnnnn nnnnnnnnnn gggrnyyycc nnnnnnnnnn      60
nnnnnnnnnn nnnnnnnnnn nnnnnnnnnn gggrnyyycc nnnnnnnnnn nnnnnnnnnn     120
nnnnnnnnnn nnnnnnnnnn gggrnyyycc nnnnnnnnnn nnnnnnnnnn nnnnnnnnnn     180
nnnnnnnnnn gggrnyyycc nnnnnnnnnn nnnnnnnnnn nnnnnnnnnn nnnnnnnnnn     240
gggrnyyycc nnnnnnnnnn nnnnnnnnnn nnnnnnnnnn nnnnnnnnnn gggrnyyycc     300
nnnnnnnnnn nnnnnnnnnn nnnnnnnnnn nnnnnnnnnn                          340

<210> SEQ ID NO 15
<211> LENGTH: 140
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
      may be absent.
<220> FEATURE:
<221> NAME/KEY: misc_feature
```

<222> LOCATION: (41)..(100)
<223> OTHER INFORMATION: k is a thymine (t) or guanine (g) nucleotide
<220> FEATURE:
<221> NAME/KEY: misc_feature
<222> LOCATION: (67)..(72)
<223> OTHER INFORMATION: n is any nucleotide
<220> FEATURE:
<221> NAME/KEY: misc_feature
<222> LOCATION: (101)..(140)
<223> OTHER INFORMATION: n is any nucleotide and up to 40 nucleotides
       may be absent.

<400> SEQUENCE: 15
nnnnnnnnnn nnnnnnnnnn nnnnnnnnnn nnnnnnnnnn ctctaatkag ctctaatkag      60
ctctaatkag ctctaatkag ctctaatkag ctctaatkag nnnnnnnnnn nnnnnnnnnn     120
nnnnnnnnnn nnnnnnnnnn                                                 140

<210> SEQ ID NO 16
<211> LENGTH: 340
<212> TYPE: DNA
<213> ORGANISM: Artificial
<220> FEATURE:
<223> OTHER INFORMATION: Synthetic DNA sequence
<220> FEATURE:
<221> NAME/KEY: misc_feature
<222> LOCATION: (1)..(40)
<223> OTHER INFORMATION: n is any nucleotide and up to 40 nucleotides
       may be absent.
<220> FEATURE:
<221> NAME/KEY: misc_feature
<222> LOCATION: (48)..(298)
<223> OTHER INFORMATION: k is a guanine (g) or thymine nucleotide
<220> FEATURE:
<221> NAME/KEY: misc_feature
<222> LOCATION: (51)..(90)
<223> OTHER INFORMATION: n is any nucleotide and up to 40 nucleotides
       may be absent.
<220> FEATURE:
<221> NAME/KEY: misc_feature
<222> LOCATION: (101)..(140)
<223> OTHER INFORMATION: n is any nucleotide and up to 40 nucleotides
       may be absent.
<220> FEATURE:
<221> NAME/KEY: misc_feature
<222> LOCATION: (151)..(190)
<223> OTHER INFORMATION: n is any nucleotide and up to 40 nucleotides
       may be absent.
<220> FEATURE:
<221> NAME/KEY: misc_feature
<222> LOCATION: (201)..(240)
<223> OTHER INFORMATION: n is any nucleotide and up to 40 nucleotides
       may be absent.
<220> FEATURE:
<221> NAME/KEY: misc_feature
<222> LOCATION: (251)..(290)
<223> OTHER INFORMATION: n is any nucleotide and up to 40 nucleotides
       may be absent.
<220> FEATURE:
<221> NAME/KEY: misc_feature
<222> LOCATION: (301)..(340)
<223> OTHER INFORMATION: n is any nucleotide and up to 40 nucleotides
       may be absent.

<400> SEQUENCE: 16
nnnnnnnnnn nnnnnnnnnn nnnnnnnnnn nnnnnnnnnn ctctaatkag nnnnnnnnnn      60
nnnnnnnnnn nnnnnnnnnn nnnnnnnnnn ctctaatkag nnnnnnnnnn nnnnnnnnnn     120
nnnnnnnnnn nnnnnnnnnn ctctaatkag nnnnnnnnnn nnnnnnnnnn nnnnnnnnnn     180

```
nnnnnnnnnn ctctaatkag nnnnnnnnnn nnnnnnnnnn nnnnnnnnnn nnnnnnnnnn      240
ctctaatkag nnnnnnnnnn nnnnnnnnnn nnnnnnnnnn nnnnnnnnnn ctctaatkag      300
nnnnnnnnnn nnnnnnnnnn nnnnnnnnnn nnnnnnnnnn                            340
```

ENGINEERED ONCOLYTIC VIRUSES CONTAINING HYPER-BINDING SITES TO SEQUESTER AND SUPPRESS ACTIVITY OF ONCOGENIC TRANSCRIPTION FACTORS AS A NOVEL TREATMENT FOR HUMAN CANCER

SEQUENCE LISTING

The Sequence Listing test file entitled "Sequence-listing_ST25" having a size of 20,116 bytes and creation date of Aug. 25, 2016, that was electronically filed with the patent application is incorporated herein by reference in its entirety.

FIELD OF THE INVENTION

One or more embodiments of the present invention relates to design of artificial, non-naturally-occurring double stranded DNA segments designed to act as decoys to bind, sequester and suppress the aberrant activity of oncogenic transcription factors that promote cancer progression and insertion of the DNA segments into the genome of selected oncolytic virus genomes to allow delivery of the DNA segments to human cancer cells providing general methods for suppressing the aberrant activity of oncogenic transcription factors that promote cancer progression.

BACKGROUND OF THE INVENTION

A fundamental problem in the treatment of cancer tumorigenesis stems from aberrant activity of various transcription factors that promote cancer progression. The aberrant expression of oncogenic transcription factors, such as high-mobility group A (HMGA) and SRY (sex determining region Y)-box 9 (SOX9), has been shown to promote cancer tumorigenesis by increasing cell proliferation decreasing cell apoptosis, and in some cases decreasing the sensitivity of cancer cells to standard of care or chemotherapy treatments.

Elevated levels of HMGA protein expression have been reported in almost every type of human cancer, including colorectal cancer, pancreatic cancer, and breast cancer. There are two forms of HMGA proteins, HMGA1 and HMGA2, which are encoded from two different genes. Both forms of HMGA are non-histone chromatin architectural transcription factors found broadly in eukaryotes. HMGA proteins are expressed at high levels in embryonic tissues during early development and at very low levels in normal differentiated somatic adult cells, except for bursts of expression during certain adaptive immune responses. Regulation of gene expression is a primary function of HMGA in these cells and HMGA proteins are involved in both positive and negative regulation of genes responsible for apoptosis, cell proliferation, immune response and DNA repair. Overexpression of HMGA has been shown to increase cell proliferation contributing to tumor growth.

It has been shown that HMGA1 interacts with the p53 tumor suppressor protein and inhibits its apoptotic activity. It has also been shown that high expression levels of HMGA1 are responsible for chemotherapy resistance in pancreatic cancer cell lines and that suppression of HMGA1 expression by siRNA restored the cells sensitivity to gemcitabine. HMGA2 is responsible for maintaining Ras-induced epithelial-mesenchymal transition that promotes tissue invasion and metastasis. Down regulation of overexpressed HMGA2 has been shown to inhibit cell proliferation in human pancreatic cancer cell lines. While the precise role that HMGA plays in cancer is not yet completely understood, HMGA has been suggested as a potential biomarker for tumor progression and is a drug target for cancer therapy development.

An early structural study showed that HMGA does not adopt a conventional protein structure composed of α helices or β sheets but rather binds in the minor groove of AT-rich double-stranded DNA through crescent-shaped DNA binding motifs referred to as "AT-hooks." In contrast to classical transcription factors that bind specific DNA sequences, HMGA acts as an architectural transcription factor that binds a specific type of DNA secondary structure, i.e. the minor groove of A:T tract DNA. Each AT-hook binds a sequence of 5-6 consecutive As, Ts, or a mixture of As and Ts, and HMGA contains three AT-hooks meaning that each HMGA protein is capable of binding three segments of 5-6 consecutive As, Ts, or mixture of As and Ts, and the segments can be separated by a spacer. Due to this unique DNA binding property of HMGA, several cancer therapy drugs, such as FR900482 and FL317, have been designed as competitive HMGA1 inhibitors that bind to the minor groove of AT-rich DNA. These drugs however, have shown high toxicity in humans. Recently, it has been shown that Spiegelmer NOX-A50 is a potent inhibitor of HMGA1 activity and proposed the use of artificial HMGA1 substrates that block HMGA1 binding to its natural DNA substrate. In principle, decreasing all HMGA protein activity could result in inhibition of unwanted cell proliferation and reestablishment of apoptosis, reducing cancer progression.

Nucleic acid ligands designed or selected to inhibit the activity of pathogenic proteins by selectively binding with and sequestering them are referred to "decoys". These decoys contain variable sequences and/or modified chemical structures to facilitate binding to their protein targets with high specificity and an equal to, or higher, affinity compared to their unmodified oligomer counterparts. They are widely studied for biotechnological and therapeutic applications because they have little or no immunogenicity compared to antibodies.

Recently, double stranded uniformly sulfur substituted phosphorothioate DNA (sDNA) aptamers oligomers containing HMGA binding sequences have been developed to sequester and suppress the oncogenic activity of HMGA1 in human cancer cells (see, U.S. Pat. No. 9,233,119 and U.S. Published Application No. US 2016/0136195, the disclosure of which is incorporated herein by reference in its entirety). The transcription factor binding site on these sDNA aptamers acts as a decoy and binds the targeted transcription factor, competing for its binding to the genomic DNA. One significant limitation with this aptamer approach is that the effect size was dose dependent, meaning that in order to increase the effect, the cells had to be treated with more aptamer molecules. There is, of course, a practical limit to the number of aptamers that can be transfected into a particular cancer cell.

Another serious limitation of the aptamer decoy approach is the difficulty in delivering the aptamers specifically to the cancer cells in a real tumor environment. Recently, oncolytic viruses have shown great potential in connection with various therapies for treating human cancers, in part due to their ability to selectively replicate in cancer cells, which ultimately leads to cancer cell lysis, while leaving healthy cells unaffected. Another attractive aspect of oncolytic viruses as potential cancer therapeutics is the ability to engineer them using modern molecular biology techniques to introduce genes or other DNA based regulatory elements into the viral genome which, when selectively replicated in cancer cells, can potentially disrupt aberrant signaling pathways. Gene therapy approaches for treating cancer are rapidly growing as alternatives to conventional or traditional.

While many oncolytic viruses are being tested, it is believed that adenovirus serotype 5 (Ad5) is the only virus that is currently approved as a drug for human cancer treatment. More than 15 oncolytic viruses are currently in clinical trials. Adenoviruses are recognized as one of the most potent vectors for gene delivery for infectious diseases and cancer. Current adenovirus vectors fall broadly into two categories: replication defective and replication competent. Replication competent adenoviruses have the advantage that the virus can be replicated in human cells, enabling up to 10,000-fold amplification of the transgenes or regulatory elements that they carry, thereby magnifying the effect of delivery of genes or DNA regulatory elements to targeted cells. However, they also produce infectious progeny that can put patients at risk of frank adenovirus infections. Replication defective vectors have been engineered by deleting their early E1 genes to disable production of infectious progeny. While replication defective viruses are safer, they produce significantly less transgene protein synthesis and copies of DNA regulatory elements because they do not undergo replication.

Accordingly, what is needed in the art is a general method to selectively suppress the action of oncogenic transcription factors in tumor cancer cells in humans. We have invented a method to engineer and insert double-stranded DNA decoy sequences capable of binding one or more targeted oncogenic transcription factors into the genome of viruses to be used as a novel cancer therapy modality. The engineered viruses offer a method for delivering novel DNA sequences to the nucleus of the cancer cells in a real tumor environment and selectively suppressing the action of oncogenic transcription factors in cancer cells in human tumors.

SUMMARY OF THE INVENTION

In one or more embodiments, an artificial, non-naturally-occurring double-stranded DNA segment is designed, created and inserted into the genome of an oncolytic or other vehicle virus to act as a decoy binding site for oncogenic transcription factors once the oncolytic or vehicle virus has infected the cancer cells. In one or more embodiments, a general method is provided allowing selective suppression of the aberrant activity of oncogenic transcription factors in cancer cells that promote cancer progression. The methods of various embodiments of the present invention include sequestration of oncogenic transcription factors at artificial, non-naturally occurring engineered transcription factor binding sites carried in the genomic DNA of engineered oncolytic viruses or other vehicle viruses introduced into the nucleus of the cancer cells using oncolytic or other vehicle viruses that can be engineered to selectively target and replicate in the cancer cells. In one or more embodiments, the present invention involves engineering novel non-naturally-occurring DNA sequences that represent "hyper-binding sites" containing one or more copies of the transcription factor binding sites for the targeted oncogenic transcription factors and incorporating the novel non-naturally-occurring DNA sequences representing the hyper-binding sites into the genome of the oncolytic viruses, and then introducing them into cancer cells by the natural process of infection of the virus used as a vehicle.

In some embodiments, the present invention takes advantage of the ability of oncolytic viruses to selectively replicate in cancer cells to deliver and amplify the number of transcription factor binding sites and/or hyper-binding sites in the nucleus of cancer cells. Once introduced into the cancer cells, these transcription factor binding sites and/or hyper-binding sites act as decoys for binding for the targeted transcription factor so as to competitively sequester oncogenic transcription factors away from the host genomic DNA, thus abolishing or reducing oncogenic transcription factor activity, resulting in restored sensitivity to chemotherapy, increased apoptosis, and reduced cancer cell proliferation. Importantly, the methods of various embodiments of the present invention are entirely general since the transcription factor binding sites and hyper-binding sites can be designed to be specific to any targeted oncogenic transcription factor and the oncolytic and other cancer specific viruses provide tissue and cell specificity, since they are engineered to selectively replicate in rapidly proliferating cancer cells.

In a first aspect, embodiments of the present invention relate to a method of treating cancer in patients by selectively suppressing the activity of oncogenic transcription factors in cancer cells comprising: identifying one or more oncogenic transcription factors to be targeted; preparing a linear double stranded DNA segment containing one or more DNA sequences that exhibit tight binding to the one or more targeted oncogenic transcription factors; inserting the linear double stranded DNA segment into the genomic DNA of a virus for delivery to cancer cells of one or more of the DNA sequences that exhibit tight binding to the targeted oncogenic transcription factors, growing, propagating, and harvesting the virus for therapeutic application; and administering the virus into a patient and allowing the virus to infect cancer cells and deliver the genomic DNA containing the linear double stranded DNA segment into the nucleus of the cancer cells, wherein one or more of the targeted oncogenic transcription factors in the cancer cells competitively bind to the one or more of the DNA sequences, rather than the genomic DNA of the cancer cell, thereby suppressing the activity of the one or more targeted oncogenic transcription factors in the cancer cell. In some embodiments, the linear double stranded DNA segment contains one or more copies of the consensus binding site for any of the one or more a targeted oncogenic transcription factors. In some embodiments, the one or more targeted oncogenic transcription factor(s) is selected from the group consisting of High Mobility Group A (HMGA), HMGA-1, HMGA-2, SRY (sex determining region Y)-box 9 (SOX9), STAT3, STAT5, Pdx1, NF-KB, and combinations thereof.

In one or more embodiments, the method for treating cancer patients of the present invention includes any one or more of the above referenced embodiments of the first aspect of the present invention wherein the virus is an oncolytic virus. In one or more embodiments, the method for treating cancer patients of the present invention includes any one or more of the above referenced embodiments of the first aspect of the present invention wherein the virus is selected from the group consisting of adenoviruses, herpes simplex virus 1 (HSV1), reovirus, vaccinia virus, vesiculostomatitis virus, and poliovirus. In some embodiments, the virus is an adenovirus.

In one or more embodiments, the method for treating cancer patients of the present invention includes any one or more of the above referenced embodiments of the first aspect of the present invention further comprising: identifying a DNA binding sequence for each one of the targeted oncogenic transcription factors that tight binds to that targeted oncogenic transcription factor; and fabricating a double stranded DNA segment containing one or more copies of each of the DNA binding sequences. In one or more embodiments, the method for treating cancer patients of the present invention includes any one or more of the above referenced embodiments of the first aspect of the present invention wherein the step of inserting the linear double stranded DNA segment into the genomic DNA of a virus further comprises: inserting one or more restriction sites into the genomic DNA of a virus; adding matching restriction sites to the ends of the linear double stranded DNA segment; and inserting the linear double stranded DNA segment into the genomic DNA of the virus by homologous recombination.

In one or more embodiments, the method for treating cancer patients of the present invention includes any one or more of the above referenced embodiments of the first aspect of the present invention wherein the step of inserting the linear double stranded DNA segment into the genomic DNA of a virus further comprises: preparing a plasmid containing the complete genome of adenovirus serotype 5 (Ad5); deleting the E1ACR2 and E1B19K genes from the Ad5 genome of the plasmid to create a replication competent double deletion mutant (Ad5ΔΔ) vector that promotes selective viral replication in cancer cells; preparing a synthetic oligomer comprising regions of overlap with the E2A and E3 regions of the Ad5ΔΔ vector, separated by a third restriction site; inserting the synthetic oligomer between the E2A and E3 regions of the Ad5ΔΔ vector amplifying the double stranded DNA sequence and incorporating it into an adenovirus shuttle plasmid; and inserting the double stranded DNA sequence into the Ad5ΔΔ vector at the third restriction site located between the E2A and E3 regions of the Ad5ΔΔ vector.

In one or more embodiments, the method for treating cancer patients of the present invention includes any one or more of the above referenced embodiments of the first aspect of the present invention further comprising combining administration of the engineered oncolytic virus to the patient with administration of a therapeutically effective amount of a chemotherapeutic agent or a pharmaceutically acceptable salt thereof to the patient. In one or more embodiments, the method for treating cancer patients of the present invention includes any one or more of the above referenced embodiments of the first aspect of the present invention wherein the step of administering is performed by intravenous, regional, intratumoral injection or inhalation. In one or more embodiments, the method for treating cancer patients of the present invention includes any one or more of the above referenced embodiments of the first aspect of the present invention wherein the chemotherapeutic agent is selected from the group consisting of gemcitabine, erlotnib hydrochloride, irinotecan, dimethylaminopathenolide, and combinations, analogs, and pharmaceutically acceptable salts thereof.

In a second aspect, the present invention is directed to a linear double stranded DNA segment engineered to contain one or more sites capable of tight binding with an oncogenic transcription factor. In some of these embodiments, the linear double stranded DNA segment is also engineered to contain one or more sites capable of tight binding with a second or more oncogenic transcription factor. In one or more embodiments, the linear double stranded DNA segment of the present invention includes any one or more of the above referenced embodiments of the second aspect of the present invention having a length of from about 6 base pairs to about 7500 base pairs. In one or more embodiments, the linear double stranded DNA segment of the present invention includes any one or more of the above referenced embodiments of the second aspect of the present invention wherein the linear double stranded DNA segment is engineered to contain two or more copies of the consensus binding site for the oncogenic transcription factor.

In one or more embodiments, the linear double stranded DNA segment of the present invention includes any one or more of the above referenced embodiments of the second aspect of the present invention wherein the linear double stranded DNA segment is engineered to contain two or more copies of a consensus binding site for two or more different oncogenic transcription factors. In one or more embodiments, the linear double stranded DNA segment of the present invention includes any one or more of the above referenced embodiments of the second aspect of the present invention wherein the linear double stranded DNA segment is engineered to containing from about 2 to about 1000 copies of the consensus binding site for the oncogenic transcription factor.

In a third aspect, the present invention is directed to a virus having a genomic DNA engineered to include the double stranded DNA sequence of the second aspect of the present invention as set forth above. In one or more embodiment, the virus is engineered to deliver the double stranded DNA sequence to the nucleus of a cancer cell. In one or more embodiments, the virus of the present invention includes any one or more of the above referenced embodiments of the third aspect of the present invention wherein the virus is engineered to preferentially replicate in cancer cells. In one or more embodiments, the virus of the present invention includes any one or more of the above referenced embodiments of the third aspect of the present invention wherein the virus is oncolytic. In one or more embodiments, the virus of the present invention includes any one or more of the above referenced embodiments of the third aspect of the present invention wherein the virus is selected from the group consisting of the families of adenoviruses, vaccinia virus, Myxoma virus, herpes simplex virus 1 (HSV1), reovirus, vaccinia virus, vesiculostomatitis virus, and poliovirus.

BRIEF DESCRIPTION OF THE DRAWINGS

For a more complete understanding of the features and advantages of the present invention, reference is now made to the detailed description of the invention along with the accompanying figures in which:

FIGS. 9A-B are an image (FIG. 9A) and graph (FIG. 9B) showing the results of a western blot analysis of HMGA-1 expression levels in three different human pancreatic cancer cell lines (from Watanabe et al., 2012).

FIGS. 10A-B are graphs showing increased sensitivity of MiaPaca-2 pancreatic cancer cells to gemcitabine following treatment with sDNA aptamers containing the HMGA1 binding site (See, Watanabe et al., 2012).

FIGS. 11A-C are images showing the cytotoxic effects caused by viral infection of: AD293 cells transfected with the pUC-GFP plasmid as a negative control (FIG. 11A); infection with AdEz virus (FIG. 11B); and infection with the Ad5-RD-HMGA-6 virus (FIG. 11C). All images were taken with 20× objective lens.

FIGS. 12A-B are images showing immunocytofluorescence assays for viral coat proteins in infected AD293 cells. FIG. 12A shows staining of AD293 cells infected with linearized native AdEz DNA. FIG. 12B shows staining of AD293 cells infected with linearized Ad5-RDHMGA-6 DNA. Assays for uninfected cells exhibited no fluorescence.

FIGS. 13A-C are images confirming viral synthesis from an engineered Ad5ΔΔ genome, according to one or more embodiments of the present invention. FIG. 13A shows staining of AD293 cells with no infection. FIG. 13B shows AD293 three days after infection with linearized Ad5ΔΔ DNA. FIG. 13C shows immunocytofluorescence staining of AD293 cells for viral proteins after infection with Ad5ΔΔ DNA.

FIGS. 14A and B represent two separate repeats of the experiment. The columns labeled "Cell Only" indirectly indicate number of MiaPaCa-2 cells at 72 hours in the absence of infection. The bars labeled "AdEz" indicate numbers of cells 72 hours after infection with the replication defective AdEz virus. The bars labeled "HMGA" indicate number of cells 72 hours after infection with the Ad5ΔΔ-RD-HMGA-6 virus.

DETAILED DESCRIPTION OF THE ILLUSTRATIVE EMBODIMENTS

Figure 1:
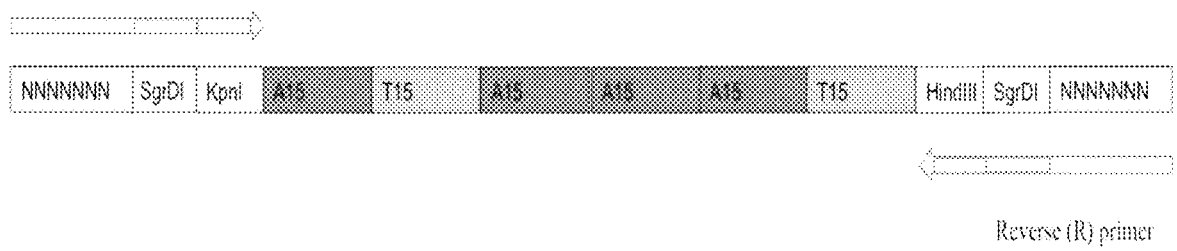
FIG. 1 is a schematic summary of the design of the HMGA-6 hyper-binding site according to one or more embodiments of the present invention.

In one or more embodiments, the present invention provides novel artificial, non-naturally-occurring double stranded DNA segments capable of acting as decoy binding sites for oncogenic transcription factors and a general method for suppressing aberrant activity of oncogenic transcription factors that promote cancer progression. In general outline, the methods of various embodiments of the present invention involve the sequestration of targeted oncogenic transcription factors at artificial, non-naturally occurring engineered transcription factor binding sites introduced into the cells using oncolytic or other viruses that can be engineered to selectively target cancer cells. These artificial, non-naturally occurring engineered transcription factor binding sites act as decoys for binding so as to competitively sequester oncogenic transcription factors away from the host genomic DNA, thus abolishing or reducing oncogenic transcription factor activity and resulting in restored sensitivity to chemotherapy, increased apoptosis, and reduced cancer cell proliferation. As will be apparent, the more copies of the engineered transcription factor binding sites introduced into the cancer cells, the more targeted oncogenic transcription factors may be sequestered away from the host genomic DNA resulting in increased suppression of the effect and action of the targeted oncogenic transcription factors. Importantly, the methods of various embodiments of the present invention are entirely general since the engineered transcription factor binding sites can be designed to be specific to any targeted oncogenic transcription factor and the oncolytic virus provides tissue and cell specificity, since they are engineered to selectively replicate in rapidly proliferating cancer cells.

As will be apparent to those of ordinary skill in the art, there are three different general approaches that may be used to increase the number of copies the engineered transcription factor binding sites present in the targeted cancer cells, all of which are contemplated by the present invention. The first approach involves increasing the dose of administration of viruses, each one having a single or small number of artificial engineered transcription factor binding sites, using a replication defective engineered virus. In these embodiments, it is preferable (but not required) to limit damage to healthy cells by administering the viruses directly to the tumor site. This approach is relatively simple and straightforward and may be of particular value in situations where the cancer cells are localized and easily accessible, there are relatively few targeted oncogenic transcription factors to be sequestered, and/or where the use a replication competent virus would be too toxic to the patient.

A second approach involves the administration of a much lower dose of the replication defective engineered viruses, but with each virus carrying a double stranded DNA segment having one or more engineered "hyper-binding sites" for the targeted oncogenic transcription factors. As used herein, the term "hyper-binding site" refers to one or more areas of the viral genome that have been engineered to contain numerous copies of the artificial double stranded DNA segments containing transcription factor binding sites for the targeted oncogenic transcription factors. As will be appreciated by those of skill in the art, this approach can provide a large number of engineered transcription factor binding sites to the cancer cells with a relatively low viral load dose compared to the first approach, and this approach is potentially valuable in cases where either the administered virus has a toxic effect or elicits a strong immune response, in cases where the use of a replication competent virus would be too toxic to the patient. In these embodiments, it is preferable (but not required) to limit damage to healthy cells by administering the viruses directly to the tumor site.

A third approach involves introduction of double stranded DNA segments having one or more engineered transcription factor binding sites and/or hyper-binding sites for the targeted oncogenic transcription factor(s) using a cancer cell selective, replication competent virus to deliver and then amplify the number of transcription factor binding sites and/or hyper-binding sites in the nucleus of cancer cells. In these embodiments, it is preferable (but not required) to limit damage to healthy cells by administering using a cancer cell specific virus. As used herein, a "cancer cell specific virus" refers to a virus that selectively replicates in rapidly dividing cancer cells. In one or more embodiments, the present invention involves incorporating one or more transcription factor binding sites (individually or as hyper-binding sites) into the genome of an oncolytic virus, and taking advantage of the oncolytic virus's ability to selectively replicate in cancer cells to deliver and amplify the number of hyper-binding sites in the nucleus of cancer cells. That is, when the engineered virus infects cancer cells, the genomic DNA of the oncolytic virus containing the transcription factor binding sites will enter the nucleus of the cancer cells, and as a normal phase of viral replication, the genomic DNA of the oncolytic virus is then replicated in the nucleus of the cancer cell, resulting in replication of the artificial engineered transcription factor binding sites as well. Once the cancer cell has been infected, there should be free viral genomic DNA, and with it transcription factor binding sites, accessible to the targeted oncogenic transcription factors in the nucleus of the cancer cells. Moreover, when the infected cancer cell dies and is lysed, these viruses will infect the neighboring cancer cells to deliver and then further amplify the number of targeted transcription factor decoy binding sites in those cancer cells as well.

As will be appreciated by those of skill in the art, traditional radiation and chemotherapy based cancer treatments have substantial side effects related to the impact of the treatments on healthy tissues due to the indiscriminate nature of such treatments. In various embodiments of the present invention, selective replication of the engineered virus in cancer cells acts to amplify the effective dose of the treatment by expansion and replication of the hyper-binding sites, without additional damage to healthy tissues and/or the side effects that would come with additional and/or larger doses of traditional radiation and chemotherapy based cancer treatments. Further, it is believed that the targeted therapies of the present invention are especially useful in situations where cancers are routinely first identified or diagnosed in a later stage of development due to asymptomatic early stage onset and progression. In addition, it is believed that this approach can also be used to treat inoperable tumors, and can be used by direct injection of the engineered oncolytic virus into the tumor to elicit its effect. Moreover, in one or more embodiments of the present invention, chimeric hyper-binding sites that combine binding sites for multiple oncogenic transcription factors into a single hyper-binding site may be fabricated, thus enabling simultaneous targeting and suppression of multiple oncogenic transcription factors.

As set forth above, cancer treatments using the engineered double stranded DNA segments and methods of the present invention focus on one or more oncogenic transcription factors that promote progression of the cancer being treated. As used herein, the term "oncogenic transcription factor" refers to a transcription factor that is expressed in elevated levels in cancer cells and/or which promotes cancer cell proliferation. In one or more embodiment of the present invention, any oncogenic transcription factors having binding sites that are known or readily discernable may be targeted for decoy attack and sequestration provided that suppression of the activity of the targeted oncogenic transcription factor to normal levels of activity is not unacceptably toxic to the patient. In one or more embodiments, the oncogenic transcription factor targeted may be a conventional transcription factor that binds to a specific double stranded DNA sequence, an architectural transcription factor, or a combination thereof.

Examples of oncogenic transcription factors suitable for targeting by various embodiments of the present invention include, without limitation, those listed in Table 1 below.

TABLE 1

Partial list of suitable oncogenic transcription factors that may be targeted by the various embodiments of the present invention.

| Oncogenic Transcription Factors | Cancer types |
| --- | --- |
| HMGA, HMGA1, HMGA2 | Pancreatic, Prostate, Colorectal, Lung, Breast, Thyroid, ovary, uterine cervix and body, prostate, gastric, and head and neck tumors |
| SOX9 | Brain, pancreatic, colorectal, lung, prostate, sarcomas, thyroid, breast, kidney |
| c-JUN | Liver, breast |
| STAT3/STAT5 | Non-small-cell lung cancer, colorectal, squamous cell carcinoma |
| NF-κB | Acute lymphoblasic leukemia, anaplastic large-cell lymphoma, breast, Burkitt lymphoma, colorectal, diffuse large B-cell lymphoma, fibrosarcoma, head and neck cancer, Hodgkin's lymphoma, mammary carcinoma, mantle cell lymphoma, melanoma, multiple myeloma, lung, ovarian, pancreatic, prostate, squamous-cell, thyroid, vulva |
| PDX1 | Pancreatic |
| Zeb1/Zeb2 | ovarian, breast, endometrium, lung, prostate, colon, gallbladder, pancreas and bladder |
| Ngn3 | Pancreatic cancer |
| neurod | Neuroendocrine and pancreatic cancer |
| Hnf6 | Pancreatic cancer |
| PAX1-PAX9 | Ovarian, breast, renal cancers |

As set forth above, more than one oncogenic transcription factor may be targeted for sequestration, and in some embodiments the engineered double stranded DNA sequences of the present invention may comprise artificial, non-naturally-occurring engineered transcription factor binding sites and/or hyper-binding sites for more than one oncogenic transcription factor. The number of different oncogenic transcription factors that may be targeted is not particularly limited but, among other factors, it will depend upon the particular virus chosen, the length of engineered double stranded DNA sequence that may be inserted into the genomic DNA of that virus, the length of the each type of engineered transcription factors binding site to be inserted, the total number to be inserted for each oncogenic transcription factor to be targeted, and the compatibility of the different binding sites. In one or more embodiments, engineered double stranded DNA sequence may contain artificial engineered transcription factors binding sites for from about 1 to about 10 different oncogenic transcription factors. In one or more embodiments, engineered double stranded DNA sequence may contain engineered transcription factors binding sites for from about 1 to about 7 different oncogenic transcription factors. In one or more embodiments, engineered double stranded DNA sequence may contain engineered transcription factors binding sites for from about 1 to about 5 different oncogenic transcription factors. In one or more embodiments, engineered double stranded DNA sequence may contain engineered transcription factors binding sites for from about 2 to about 10 different oncogenic transcription factors. In one or more embodiments, engineered double stranded DNA sequence may contain engineered transcription factors binding sites for from about 4 to about 10 different oncogenic transcription factors. In one or more embodiments, engineered double stranded DNA sequence may contain engineered transcription factors binding sites for from about 2 to about 8 different oncogenic transcription factors. In one or more embodiments, engineered double stranded DNA sequence may contain engineered transcription factors binding sites for from about 2 to about 6 different oncogenic transcription factors.

Once the oncogenic transcription factors to be targeted for treatment have been identified, at least one site and specific DNA sequences in the genomic DNA of the cancer cell to which each targeted oncogenic transcription factors bind must then be identified for each targeted oncogenic transcription factor. As used herein, the terms "oncogenic transcription factor binding site," "transcription factor binding site," and "binding site" are used interchangeably to refer to a specific sequence of DNA base pairs to which a particular oncogenic transcription factor binds with high affinity, whether synthetic or naturally occurring. Similarly, the terms "engineered oncogenic transcription factor binding site," "engineered transcription factor binding site," and "engineered binding site" as used herein, refer to an engineered series of DNA nucleotides that is designed to bind to a particular oncogenic transcription factor with an affinity greater than or equal to that of the naturally occurring transcription factor binding site, which have been synthesized for insertion into cancer cells and are not naturally occurring. As will be appreciated by those of skill in the art, binding sites for many oncogenic transcription factors are known and, and where they are not already known, they can be readily identified by those of ordinary skill in the art without undue experimentation. In one or more embodiments, the binding site for a targeted oncogenic transcription factors will be the consensus binding site for that oncogenic transcription factor, but this need not be the case. The binding site may be any DNA sequence found in the genome of the targeted cancer cells that exhibits tight binding to that oncogenic transcription factor.

As used herein, the terms "tight binding" or "[to] tight bind" refer to binding with the transcription factor that is at least as tight as that of the consensus binding site as measured by the dissociation constant $K_d$. Similarly, a binding site may be said to be "capable of tight binding" where the targeted transcription factor will bind to that binding site at least as tightly as it would to its consensus binding site under substantially the same conditions, as measured by the dissociation constant $K_d$. When referring to a transcription factor DNA binding segment, the terms "consensus binding sequence" or "consensus binding site" are used herein to refer to a sequence of nucleotides in a DNA segment of defined length and sequence composition that is determined to be required for specific binding by the transcription factor in comparison to its non-specific binding to a segment of DNA of random length and nucleotide composition. The "consensus binding sequence" or "consensus binding site" is determined by comparing the minimal DNA sequence length and composition required for specific binding site for the transcription factor in the genome of multiple individuals or organisms in order to determine the minimally conserved DNA sequence length and composition that is required for specific binding by the transcription factor. The "consensus binding sequence" or "consensus binding site" may contain some nucleotide positions that are invariant and strictly required for specific binding, and it may contain certain nucleotide positions that are variable and not strictly required for specific binding. The number of nucleotides spanning and including the strictly required nucleotides defines the length of the "consensus binding sequence" or "consensus binding site".

Once the binding site of the oncogenic transcription factor has been identified, the design of an engineered double stranded DNA segment having one or more binding sites for the one or more targeted oncogenic transcription factors may be developed and the double stranded DNA segment fabricated by any method known in the art for that purpose. Synthesis of custom double stranded DNA segments has become routine and one of ordinary skill in the art will be able to synthesize or purchase double stranded DNA segments according to one or more embodiments of the present invention without undue experimentation. Alternatively, suitable double stranded DNA segments may be custom synthesized by a variety of commercial vendors, including by way of example, Integrated DNA Technologies of Coralville, Iowa (USA).

As set forth above, the maximum length of the engineered double stranded DNA segments of the present invention will be limited to lengths that can be inserted into the genomic DNA of the virus being used for delivery to the cancer cells, without significantly affecting the ability of the virus to enter the nucleus of the cancer cells, and in some embodiments, replicate. This will, in turn, depend upon such things as size of the particular virus chosen, the size of the genomic DNA of that virus, and, particularly if the virus is replication competent, the length of insert that can be accommodated without interfering with transcription and other necessary processes.

In some embodiments, the engineered double stranded DNA segments used in the present invention may be from about 6 base pairs to about 7500 base pairs in length. In some embodiments, the engineered double stranded DNA segments used in the present invention may be from about 6 base pairs to about 4000 base pairs in length. In some embodiments, the engineered double stranded DNA segments used in the present invention may be from about 6 base pairs to about 3000 base pairs in length. In some embodiments, the engineered double stranded DNA segments used in the present invention may be from about 6 base pairs to about 2000 base pairs in length. In some embodiments, the engineered double stranded DNA segments used in the present invention may be from about 50 base pairs to about 7500 base pairs in length. In some embodiments, the engineered double stranded DNA segments used in the present invention may be from about 1000 base pairs to about 7500 base pairs in length. In some embodiments, the engineered double stranded DNA segments used in the present invention may be from about 2000 base pairs to about 7500 base pairs in length. In some embodiments, the engineered double stranded DNA segments used in the present invention may be from about 3000 base pairs to about 7500 base pairs in length. In some embodiments, the engineered double stranded DNA segments used in the present invention may be from about 50 base pairs to about 2000 base pairs in length.

As set forth above, the engineered double stranded DNA segments of the present invention may contain from one to about 1000 engineered transcription factor binding sites. In some other embodiments, the engineered double stranded DNA segments of the present invention may contain from one to about 800 engineered transcription factor binding sites. In some other embodiments, the engineered double stranded DNA segments of the present invention may contain from one to about 600 engineered transcription factor binding sites. In some other embodiments, the engineered double stranded DNA segments of the present invention may contain from one to about 400 engineered transcription factor binding sites. In some other embodiments, the engineered double stranded DNA segments of the present invention may contain from 2 to about 1000 engineered transcription factor binding sites. In some other embodiments, the engineered double stranded DNA segments of the present invention may contain from 100 to about 1000 engineered transcription factor binding sites. In some other embodiments, the engineered double stranded DNA segments of the present invention may contain from 300 to about 1000 engineered transcription factor binding sites. In some other embodiments, the engineered double stranded DNA segments of the present invention may contain from 5 to about 200 engineered transcription factor binding sites. In some other embodiments, the engineered double stranded DNA segments of the present invention may contain from 5 to about 100 engineered transcription factor binding sites.

As set forth above, the engineered double stranded DNA segments of the present invention may contain one or more hyper-binding sites. In some embodiments, each hyper-binding site will contain from about 2 to about 1000 copies of a binding site for an oncogenic transcription factor being targeted. In some embodiments, each hyper-binding site will contain from about 2 to about 800 copies of a binding site for the oncogenic transcription factor being targeted. In some embodiments, each hyper-binding site will contain from about 2 to about 600 copies of a binding site for an oncogenic transcription factor being targeted. In some embodiments, each hyper-binding site will contain from about 2 to about 200 copies of a binding site for an oncogenic transcription factor being targeted. In some embodiments, each hyper-binding site will contain from about 2 to about 100 copies of a binding site for an oncogenic transcription factor being targeted. In some embodiments, each hyper-binding site will contain from about 2 to about 50 copies of a binding site for an oncogenic transcription factor being targeted. In some embodiments, each hyper-binding site will contain from about 2 to about 25 copies of a binding site for an oncogenic transcription factor being targeted. In some embodiments, each hyper-binding site will contain from about 5 to about 100 copies of a binding site for an oncogenic transcription factor being targeted.

As set forth above, the engineered double stranded DNA segments of the present invention may contain engineered transcription factor binding sites and/or hyper-binding sites for more than one different oncogenic transcription factor. In one or more embodiments of the present invention, the engineered double stranded DNA segments of the present invention may contain engineered transcription factor binding sites and/or hyper-binding sites for from 1 to about 10 oncogenic transcription factors. In some embodiments, the engineered double stranded DNA segments of the present invention may contain engineered transcription factor binding sites and/or hyper-binding sites for from 1 to about 8 oncogenic transcription factors. In some embodiments, the engineered double stranded DNA segments of the present invention may contain engineered transcription factor binding sites and/or hyper-binding sites for from 1 to about 6 oncogenic transcription factors. In some embodiments, the engineered double stranded DNA segments of the present invention may contain engineered transcription factor binding sites and/or hyper-binding sites for from 1 to about 4 oncogenic transcription factors. In some embodiments, the engineered double stranded DNA segments of the present invention may contain engineered transcription factor binding sites and/or hyper-binding sites for from 2 to about 5 oncogenic transcription factors.

In some embodiments, some or all of the engineered transcription factor binding sites and/or hyper-binding sites may be separated from each other by one or more spacers. As used herein, the term "spacer" refers to a sequence of DNA located between two engineered transcription factor binding sites to which the transcription factor does not bind. In various embodiments of the present invention, spacers may be used to optimize the number of feasible binding locations on the engineered double stranded DNA segment. In some embodiments, a spacer may be from about 1 to about 40 base pairs in length, in other embodiments, from 1 to about 30 base pairs in length, in other embodiments, from 1 to about 20 base pairs in length, in other embodiments, from 1 to about 10 base pairs in length, in other embodiments, from 10 to about 40 base pairs in length, in other embodiments, from 20 to about 40 base pairs in length, in other embodiments, from 30 to about 40 base pairs in length, and in other embodiments, more than 40 base pairs in length.

In some embodiments, hyper-binding sites according to the present invention may be one or more of those set forth in Table 2, below.

TABLE 2

Partial List of Potential Hyper Binding Sites

| Oncogenic Transcription Factor | SEQ. ID No. | Hyper-Binding Site Sequence |
|---|---|---|
| HMGA1 | 1 | $(X)_n$ AAAAAAAAAAAAAAA TTTTTTTTTTTTTTT AAAAA AAAAAAAAAAAAAAA AAAAAAAAAAAAAAA AAAAAAAAAA TTTTTTTTTTTTTTT $(X)_n$, where $(X)_n$ indicates a spacer sequence of n nucleotides of any composition.<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| HMGA1 | 2 | $(X)_n$ WWWWWWWWWWWWWWW WWWWWWWWWWWWWW WW WWWWWWWWWWWWWWW WWWWWWWWWWWWWW WWW WWWWWWWWWWWWWWW WWWWWWWWWWWWWW WWW $(X)_n$, where $(X)_n$ indicates a spacer sequence of n nucleotides of any composition and W is an thymine (T) or an adenine (A).<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| HMGA1 | 3 | $(X)_n$ AAAAAAAAAAAAAAA $(X)_n$ TTTTTTTTTTTTTTT $(X)_n$ AAAAAAAAAAAAAAA $(X)_n$ AAAAAAAAAAAAAAA $(X)_n$ AAAAAAAAAAAAAA $(X)_n$ TTTTTTTTTTTTTTT $(X)_n$, where $(X)_n$ indicates a spacer sequence of n nucleotides of any composition.<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| HMGA1 | 4 | $(X)_n$ WWWWWWWWWWWWWWW $(X)_n$ WWWWWWWWWW WWWWWW $(X)_n$ WWWWWWWWWWWWWWWW $(X)_n$ WWWWW WWWWWWWWWWWW $(X)_n$ WWWWWWWWWWWWWWWWW $(X)_n$ WWWWWWWWWWWWWWWW $(X)_n$, where $(X)_n$ indicates a spacer sequence of n nucleotides of any composition and W is an thymine (T) or an adenine (A).<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| SOX9 | 5 | $(X)_n$ AGAACAATGGAGAACAATGGAGAACAATGGAGAACAATGGA GAACAATGGAGAACAATGG $(X)_n$, where $(X)_n$ indicates a spacer sequence of n nucleotides of any composition. |

TABLE 2-continued

Partial List of Potential Hyper Binding Sites

| Oncogenic Transcription Factor | SEQ. ID No. | Hyper-Binding Site Sequence |
|---|---|---|
| | | In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| SOX9 | 6 | $(X)_n$ AGAACAATGG $(X)_n$ AGAACAATGG $(X)_n$ AGAACAATGG $(X)_n$ AGAACAATGG $(X)_n$ AGAACAATGG $(X)_n$ AGAACAATGG $(X)_n$, where $(X)_n$ indicates a spacer sequence of n nucleotides of any composition.<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| c-JUN | 7 | $(X)_n$ TGACTCA TGACTCA TGACTCA TGACTCA TGACTCA TGACTCA $(X)_n$, where $(X)_n$ indicates a spacer sequence of n nucleotides of any composition.<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| c-JUN | 8 | $(X)_n$ TGACTCA $(X)_n$ TGACTCA $(X)_n$ TGACTCA $(X)_n$ TGACTCA $(X)_n$ TGACTCA $(X)_n$ TGACTCA $(X)_n$ where $(X)_n$ indicates a spacer sequence of n nucleotides of any composition.<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| STAT-3 | 9 | $(X)_n$ TT(N4)AA TT(N4)AA TT(N4)AA TT(N4)AA TT(N4)AA TT(N4)AA $(X)_n$, where (N4) indicates a spacer of four nucleotides of any composition and $(X)_n$ indicates a spacer sequence of n nucleotides of any composition.<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| STAT-3 | 10 | $(X)_n$ TT(N4)AA $(X)_n$ TT(N4)AA $(X)_n$ TT(N4)AA $(X)_n$ TT(N4)AA $(X)_n$ TT(N4)AA $(X)_n$ TT(N4)AA $(X)_n$, where (N4) indicates a spacer of four nucleotides of any composition and $(X)_n$ indicates a spacer sequence of n nucleotides of any composition.<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| STAT-3 | 11 | $(X)_n$ TT(N5)AA TT(N5)AA TT(N5)AA TT(N5)AA TT(N5)AA TT(N5)AA $(X)_n$, where (N5) indicates a spacer of five nucleotides of any composition and $(X)_n$ indicates a spacer sequence of n nucleotides of any composition.<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| STAT-3 | 12 | $(X)_n$ TT(N5)AA $(X)_n$ TT(N5)AA $(X)_n$ TT(N5)AA $(X)_n$ TT(N5)AA $(X)_n$ TT(N5)AA $(X)_n$ TT(N5)AA $(X)_n$, where $(X)_n$ indicates a spacer sequence of n nucleotides and (N5) indicates a spacer of five nucleotides of any composition.<br>In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |

TABLE 2-continued

Partial List of Potential Hyper Binding Sites

| Oncogenic Transcription Factor | SEQ. ID No. | Hyper-Binding Site Sequence |
|---|---|---|
| NF-KB | 13 | $(X)_n$ GGGRNYYYCC GGGRNYYYCC GGGRNYYYCC GGGRNYYYCC GGGRNYYYCC GGGRNYYYCC $(X)_n$, where R is a purine (G or A), Y is a pyrimidine (T or C), N is any nucleotide, and $(X)_n$ indicates a spacer sequence of n nucleotides of any composition. In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| NF-KB | 14 | $(X)_n$ GGGRNYYYCC $(X)_n$ GGGRNYYYCC $(X)_n$ GGGRNYYYCC $(X)_n$ GGGRNYYYCC $(X)_n$ GGGRNYYYCC $(X)_n$ GGGRNYYYCC $(X)_n$, where R is a purine (G or A), Y is a pyrimidine (T or C), N is any nucleotide, and $(X)_n$ indicates a spacer sequence of n nucleotides of any composition. In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| PDX1 | 15 | $(X)_n$ CTCTAATKAG CTCTAATKAG CTCTAATKAG CTCTAATKAG CTCTAATKAG CTCTAATKAG $(X)_n$, where K is a thymine (T) or guanine (G) nucleotide, and $(X)_n$ indicates a spacer sequence of n nucleotides of any composition. In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |
| PDX1 | 16 | $(X)_n$ CTCTAATKAG $(X)_n$ CTCTAATKAG CTCTAATKAG $(X)_n$ CTCTAATKAG $(X)_n$ CTCTAATKAG $(X)_n$ CTCTAATKAG $(X)_n$, where K is a thymine (T) or guanine (G) nucleotide, and $(X)_n$ indicates a spacer sequence of n nucleotides of any composition. In some embodiments, n may be an integer from 0 to about 40, in other embodiments, from 0 to about 30, in other embodiments, from 0 to about 20, in other embodiments, from 0 to about 10, in other embodiments, from 10 to about 40, in other embodiments, from 20 to about 40, and in other embodiments, from 30 to about 40. |

Further, as will be appreciated by those of ordinary skill in the art, the ends of the engineered double stranded DNA segments of the present invention may contain one or more restriction sites to facilitate introduction of the engineered double stranded DNA segment into a shuttle vector and/or the viral genome. The specific restriction sites which may be used will depend upon the particular virus and/or shuttle plasmid chosen, but as should be apparent, the restriction sites chosen must not be present in the engineered double stranded DNA segment being inserted or in the remainder of the genomic DNA of the virus and/or shuttle plasmid being used. In one or more embodiments, restriction sites used in the initial vector may include, without limitation, KpnI, HindIII, SgrDI. See, FIG. 1.

In some embodiments, the binding site may be a HMGA hyper-binding site containing six tandem 15-base pair binding sites (HMGA-6) as shown and summarized in FIG. 1 and discussed in more depth in the Experimental section below. Each of the six 15-base pair binding sites contains a run of 15 consecutive adenine residues reading in either the forward or reverse direction, so both segments have sufficient length to achieve the narrow minor groove structure required for tight HMGA binding. In some embodiments, the synthetic 148 base pair linear DNA segment shown in FIG. 1 may obtained commercially, for example from Integrated DNA technologies, Coralville, Iowa. It should be appreciated that the flanking KpnI and HindIII restriction sites (FIG. 1) were designed to enable cutting of the HMGA hyper-binding site as required for ligation into a shuttle vector in preparation for homologous recombination to insert the HMGA hyper-binding site into the vector for the replication defective Ad5. The flanking SgrDI restriction sites were engineered to allow preparation of the HMGA hyper-binding sites for insertion into the vector containing the intact Ad5ΔΔ genome.

Once these double stranded DNA segments containing one or more transcription factor binding sites (individually or as hyper-binding sites) and the necessary restriction sites have been synthesized, various embodiments of the present invention provide one or more methods for delivering these engineered double stranded DNA segments, and with them engineered transcription factor binding sites and/or hyper-binding sites, into the nucleus of cancer cells in a real tumor environment. The engineered DNA segments may be delivered to the targeted cancer cells (preferably without harming other healthy cells) and then introduced into the nucleus of those cancer cells using any suitable method known in the art for that purpose. In one or more embodiments, a virus may be used as a vector to introduce the engineered DNA segments into the cancer cells. In one or more embodiments, cancer cell specific viruses may be used as a vector to introduce the engineered DNA segments into the cancer cells. In one or more embodiments, engineered viruses can be cancer cell specific by engineering the virus to introduce tumor specific promoters in front of essential genes for replication in the viral genome.

As set forth above, oncolytic viruses have recently been developed that have the ability to selectively replicate in cancer cells, in some cases leading to cancer cell lysis, while leaving healthy cells unaffected. And, in some embodiments of the present invention, these engineered double stranded DNA segments are selectively introduced into the nucleus of cancer cells using an oncolytic virus delivery system that acts synergistically with the lytic activity of the oncolytic virus. In some other embodiments, the engineered oncolytic viruses can be used in combination with existing alternative chemotherapy approaches. Others have demonstrated the potential benefits of combining the use of a replication competent herpes virus with gemcitabine. Another strategy of combination therapy is the use of multiple engineered oncolytic viruses. In various embodiments of the present invention, multiple engineered oncolytic viruses targeting distinct oncogenic transcription factors can be combined to synergistically enhance the efficacy of individual engineered oncolytic viruses.

In one or more embodiments of the present invention, any vehicle/oncolytic virus having a double stranded DNA genome that is capable of transfecting a DNA sequence comprising one or more binding sites/hyper-binding sites into a cancer cells, without damaging healthy tissue may be used. Of the more than a dozen oncolytic viruses currently undergoing clinical trials, those oncolytic viruses that are suitable for the approach described herein must contain double-stranded DNA genomic DNA, and these include, without limitation, vaccinia virus, Myxoma virus, adenoviruses, herpes simplex virus 1 (HSV1), reovirus, vaccinia virus, vesiculostomatitis virus, and laboratory-engineered poliovirus. In some embodiments, the oncolytic virus may be an adenovirus. Adenovirus is a widely used vector for cancer gene therapy and adenovirus associated viruses are rapidly growing as vectors for cancer gene therapy. In some embodiments, the oncolytic virus may be adenovirus serotype 5 (Ad5). There are more than 100 known serotypes of adenovirus and in general any of these serotypes are potentially suitable.

In some embodiments, the oncolytic virus may be a double deletion mutant (Ad5ΔΔ) of the adenovirus serotype 5 (Ad5) virus, which has been engineered to optimize selective replication in cancer cells. It is known that the Ad5 genome can be modified to increase specificity for replication in rapidly dividing cancer cells by deleting the E1ACR2 and E11319K genes from the Ad5 genome. In these embodiments, the E1ACR2 gene encodes a protein responsible for binding and inactivation of retinoblastoma protein (pRb), a tumor suppressor protein that prevents excessive cell growth and is dysfunctional in many cancers. When the E1ACR2 gene is deleted from the Ad5 genome, the Ad5 virus cannot replicate in cells with functioning pRb. Cancer cells often lack pRb and therefore, an Ad5 virus lacking E1ACR2 can only replicate in cancer cells and not in normal cells. Further, it is known that the second gene, E1B19K, encodes a protein that disrupts the tumor suppressor protein p53 pathway for apoptosis in human cells, allowing replication in normal cells expressing p53. Here again, tumor cells are commonly deficient in p53 and the deletion of the E1B19K gene in the Ad5 vector allows the Ad5 virus to replicate in cancer cells that are not expressing p53, but not in normal cells that are expressing p53. As E1B19K prevents apoptosis by death receptor and p53 pathways, its deletion has been found to promote apoptosis and viral spread in cancer cells.

While oncolytic viruses present significant advantages as vectors for delivery of the engineered transcription factor binding sites and/or hyper-binding sites to the nucleus of target cancer cells, the present invention is not so limited. The oncolytic characteristics of the virus, while beneficial, are not of particular importance to the practice of the present invention. Of particular importance to various embodiments of the present invention is the ability of these viruses to specifically target the cancer cells where the oncogenic transcription factors are being produced, and not damage healthy cells. As used herein, the ability of a virus to "specifically target" cancer cells refers to the ability of the virus to selectively replicate in rapidly dividing cancer cells.

As set forth above, it is believed that the sequestration of oncogenic transcription factors at artificial engineered transcription factor binding sites and/or hyper-binding sites results in restored sensitivity to chemotherapy, increased apoptosis, and reduced cell proliferation. These factors, it is believed, will result in the eventual death of the cancer cell, and it is not necessary for the oncolytic action of the virus itself to actually kill the targeted cancer cell. Accordingly, embodiments where a non-oncolytic virus is used to deliver the engineered transcription factor binding sites and/or hyper-binding sites to the nucleus of target cancer cells are possible, provided that the virus chosen has the ability of these viruses to specifically target cancer cells where the oncogenic transcription factors are being produced, has double stranded DNA, and is capable of delivering the hyper-binding sites to the nucleus of target cancer cells.

The engineered double stranded DNA segments containing the artificial engineered transcription factor binding sites and/or hyper-binding sites may be introduced into the oncolytic virus vectors using any suitable method known in the art for that purpose. Various methods for transferring synthesized double stranded DNA segments into viral vectors are well known in molecular biology and the particular techniques required will depend upon the particular engineered double stranded DNA segments (containing engineered transcription factor binding site and/or hyper-binding site) and oncolytic/vehicle virus selected. In one or more embodiments, the engineered double stranded DNA segments containing the artificial engineered transcription factor binding sites and/or hyper-binding sites may be the HMGA-6 DNA segments shown and described in FIG. 1, which contains six 15-base pair HMGA binding sites flanked by KpnI, HindIII, and SgrDI restriction sites.

It should be appreciated that the flanking KpnI and HindIII restriction sites (FIG. 1) in these embodiments are designed to enable cutting of the linear synthetic DNA segments containing the HMGA-6 DNA hyper binding sites as required for ligation into a shuttle vector in preparation for homologous recombination to insert the HMGA hyper-binding site into the vector for the replication defective Ad5 and the flanking SgrDI restriction sites are engineered to allow preparation of the HMGA hyper-binding sites for insertion into the vector containing the intact Ad5ΔΔ genome.

The virus containing the artificial engineered transcription factor binding sites and/or hyper-binding sites may be grown, propagated, and harvested for therapeutic application using conventional molecular biology methodology.

In the embodiments shown, the plasmid encoding the replication defective Ad5 virus contains all but the E1 and E3 gene regions of the intact Ad5 genome, and deletion of the E1 and E3 prevent its replication. It is known that deletion of the E1 and E3 gene regions prevents replication, i.e. it is replication defective. In some of these embodiments, the replication defective pADEasy1 plasmid in *E. coli* BJ5183 commercially available from Agilent Technologies Inc. (Santa Clara, Calif.) (See, http://www.agilent.com/cs/library/usermanuals/public/240009.pdf, the disclosure of which is incorporated herein by reference) can be used in conjunction with the pShuttle-CMV system to introduce DNA elements such as the HMGA-6 or other hyper-binding sites into the replication defective oncolytic viral genome. (See, FIG. 1 and FIG. 2). In the embodiments, the pShuttle-CMV plasmid contains a multiple cloning site sandwiched between the cytomegalovirus promoter (CMV promoter) and the SV40 polyadenylation signal, and as a result is suitable for insertion of large cDNA segments of up to 6.6 kb, which can be expressed in human cells under the control of the CMV promoter. In these embodiments, active replication of the AdEasy1 virus requires isolation of the pADEasy1 plasmid from its *E. coli* host, cutting the replication defective viral genome from the plasmid, and transformation of the linearized replication defective engineered viral genome into human embryonic kidney 293 (HEK 293 or AD 293) cells engineered to contain the complementary genes deleted from the Ad5 genome required for replication. This enables replication of the virus in the modified HEK 293 cells. In these embodiments, plaques isolated from HEK 293 cells infected with the replication defective oncolytic virus on semisolid media for human cell growth.

Figure 3:
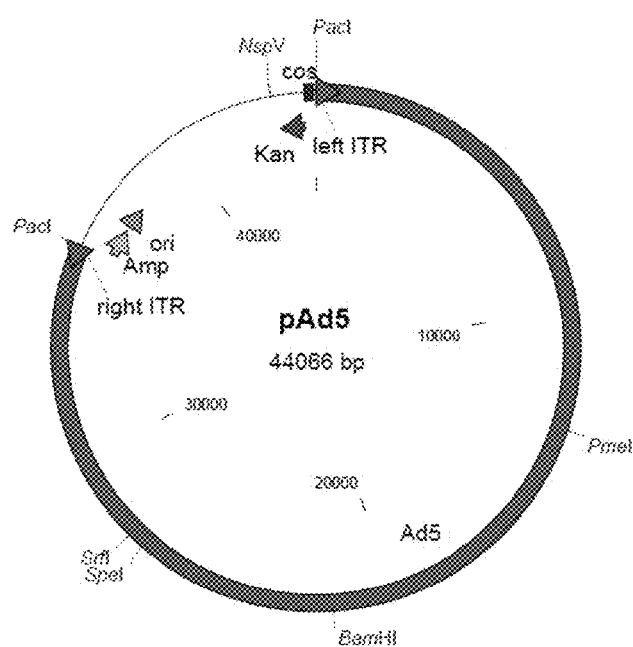
FIG. 3 is a schematic showing a pAd5 plasmid vector containing the full length Ad5 genome. Image reproduced from O.D.260, Inc. (http://www.od260.com/prod.adenovirus.pAd5.php)
Figure 4:
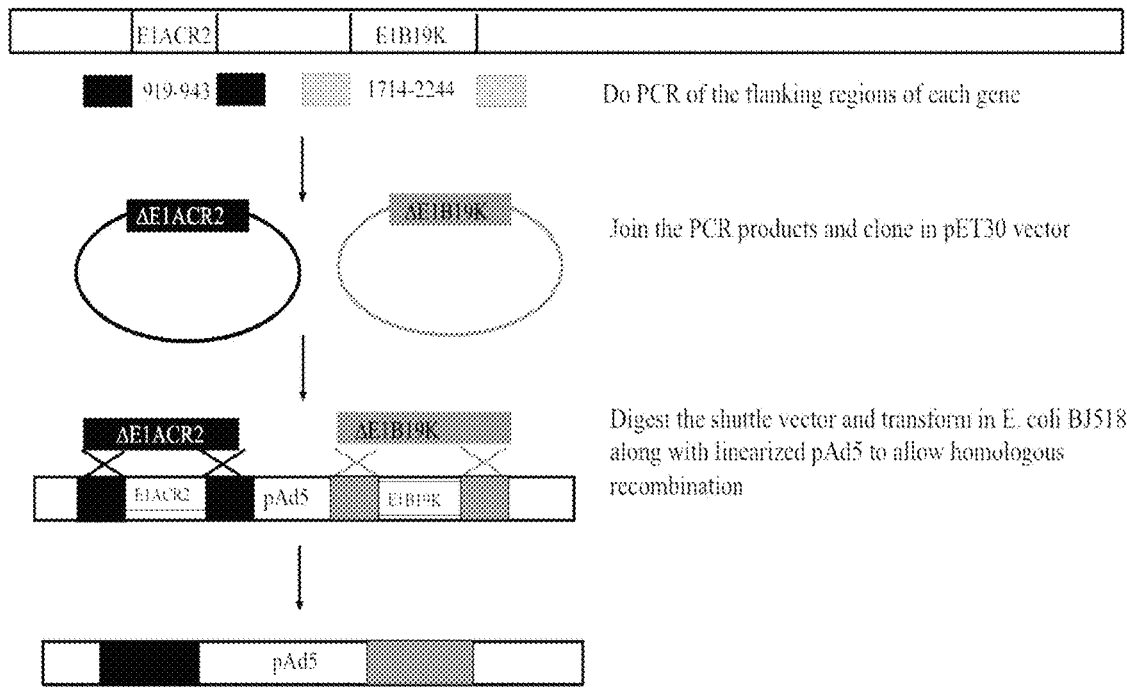
FIG. 4 is a schematic overview showing a strategy used to engineer the Ad5 viral genome to delete the E1ACR2 and E1B19K genes according to one or more embodiments of the present invention. Deletion of these two genes promotes selective replication of viral particles in rapidly dividing cancer cells and promotes spread of the virus only in rapidly dividing cancer cells.

As set forth above, a method for creating a double mutant (Ad5ΔΔ) starting from the pAd5 vector containing the full intact genome has been successfully developed. In these embodiments, the process begins with a pAd5 plasmid that contains the complete Ad5 genome (See, FIG. 3). The double deletion mutant of the Ad5 genome (Ad5ΔΔ) has been demonstrated to selectively replicate in rapidly dividing cancer cells (See, Oberg et al. "Improved potency and selectivity of an oncolytic E1ACR2 and E1B19K deleted adenoviral mutant in prostate and pancreatic cancers" *Clin Cancer Res* 16(2), 541-553, 2010), the disclosure of which is incorporated by reference herein in its entirety). As discussed above, this specificity is accomplished by deleting the E1ACR2 and E1B19K genes from the Ad5 genome. FIG. 4 shows an overview of how we engineered the double-deletion mutant of Ad5 viral genome lacking E1ACR2 and E1B19K, (i.e. Ad5ΔΔ). In these embodiments, homologous recombination is used to substitute DNA segments lacking each gene (carried on a shuttle plasmid) for the intact genomic sequence carried in a plasmid harboring the entire Ad5 genome (FIG. 3).

Figure 5:
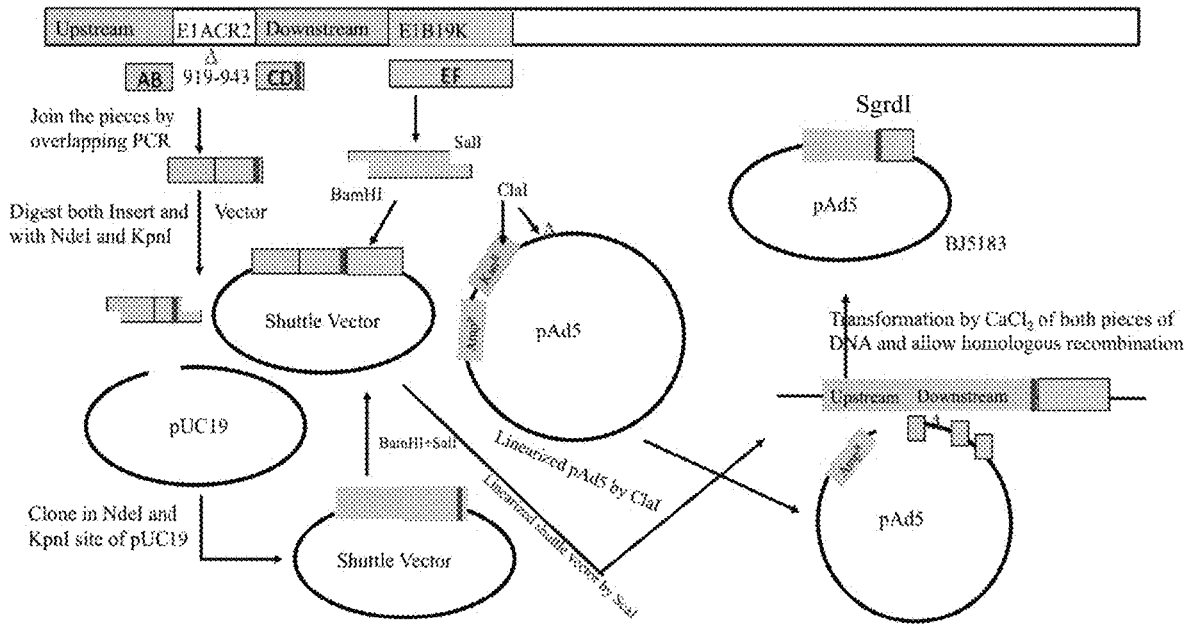
FIG. 5 is a schematic diagram illustrating a design strategy for making Ad5 double deletion mutant lacking E1ACR2, according to one or more embodiments of the present invention. The solid block indicates introduction of the SgrDI restriction enzyme site to be used for deletion of E1B19K.

A more detailed schematic is shown in FIG. 5. All primers were designed to ensure that the proper reading frame would be maintained after homologous recombination. In these embodiments, the Ad5ΔΔ vector may be generated in two steps (See, FIG. 5). In some of these embodiments, PCR primers were designed to amplify DNA flanking either side of the E1ACR2 gene from the pAd5 plasmid and to add a NdeI restriction site at the 5' end of the gene and a KpnI restriction site at the 3' side of the gene. The sequences of the PCR primer or primers used must not be present either in the artificially designed transcription factor binding sequences or in the remaining virus genome. One of ordinary skill in the art will be able to select a PCR primer without undue experimentation.

In these embodiments, the amplified "AB" PCR product for the upstream region of the E1ACR2 gene indicates the upstream sequence of DNA amplified by the A and B primer pair, where the forward primer was named "A" and the reverse primer was named "B". In the embodiment shown in FIG. 5, a SgrDI restriction site was introduced at the 3' end of the CD product (solid line) via a primer such as to enable subsequent linearization of the shuttle plasmid for the final homologous recombination step (See FIG. 5). All of the AB, CD, EF, GL, and KL products were successfully generated and confirmed by sequencing. In some of these embodiments, overlapping per was used to join the AB and CD products and the product successfully incorporated into the pCU19 shuttle plasmid. Appropriate primers, may be designed and used to amplify the E1B19K gene region and to introduce BamHI and SalI restriction sites into the EF product (See, FIG. 5). In the embodiments shown in FIG. 5, the BamH1 abdSa1I enzymes were used to cut both the shuttle plasmid carrying the ABCD product (the BamHI site is downstream of the ABCD product) and the EF product, enabling joining into another shuttle plasmid.

In these embodiments, the shuttle vector was linearized using a ScaI site and the pAd5 vector using the ClaI site. Transformation of both linearized DNAs into BJ5183 in these embodiments led to homologous recombination resulting in the shuttle plasmid carrying the E1ACR2 deletion mutant, pAd5ΔE1ACR2 (See, FIG. 5). The successful homologous recombination product loses its kanamycin resistance gene and only retains ampicillin resistance.

Figure 6:
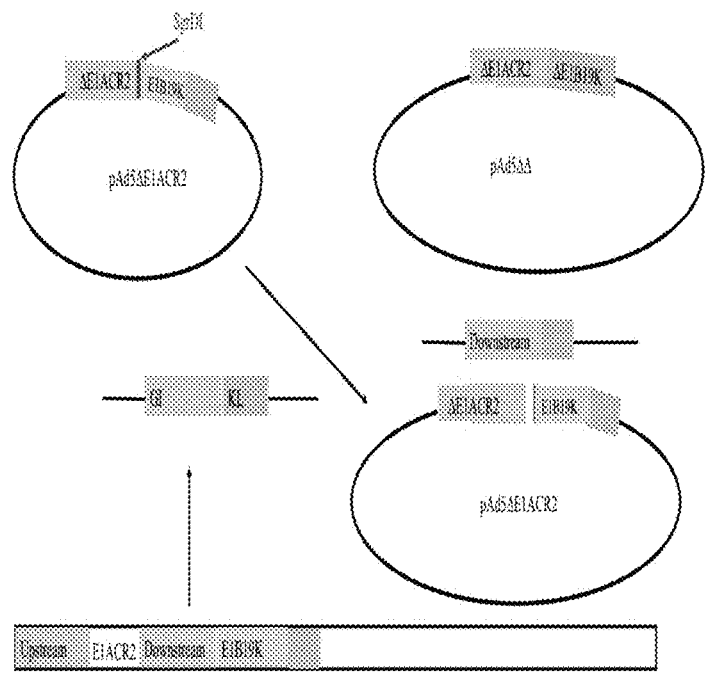
FIG. 6 is a schematic showing a strategy for deletion of E1B19K gene, according to one or more embodiments of the present invention.
Figure 7:
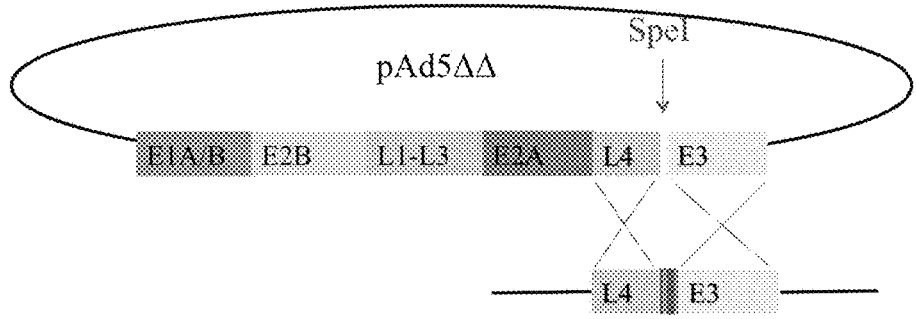
FIG. 7 is a schematic diagram showing homologous recombination used to introduce the SgrDI restriction site in between the E2A and E3 regions to allow insertion of HMGA hyper-binding sites, according to one or more embodiments of the present invention.

A strategy for deleting the E1B19K gene is summarized in FIG. 6. In these embodiments, the pAd5-E1ACR2 product from FIG. 5 was linearized with the SgrDI restriction enzyme, but the invention is not so limited and other restriction enzymes, including without limitation. A per product containing DNA sequence flanking, but lacking, the E1B19K gene, was generated using the GI and KL primer sets and used for homologous recombination with the pAd5ΔE1ACR2 plasmid (FIG. 5 and FIG. 6) resulting in a plasmid containing the desired pAd5ΔΔ double deletion mutant. The pAD5 genome has a naturally occurring SpeI site between the E2 and E3 gene regions (See, FIG. 7).

Figure 8:
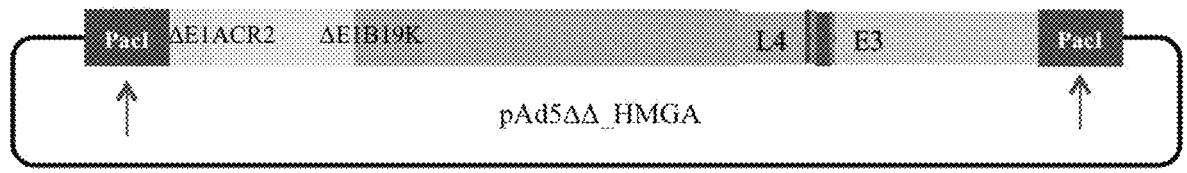
FIG. 8 is a schematic diagram showing final processing of pAd5 to prepare linearized engineered Ad5 viral genome for transformation into HEK293 cells, according to one or more embodiments of the present invention.
Figure 8:

In one or more of these embodiments, a DNA sequence containing regions of overlap with the E2A and E3 regions separated by a SgrDI restriction site was designed and commercially obtained. (See, FIG. 7) The pAd5ΔΔ vector can be linearized using a naturally occurring SpeI between E2A and E3. Transformation into BJ5183 will allow homologous recombination with a product containing flanking regions to the SpeI site and containing the SgrDI sequence (FIG. 7) to enable insertion of the engineered hyper-binding sites (FIG. 8). Finally, the pAd5ΔΔ plasmid is cut and linearized from the pAd5 plasmid using the PacI restriction sites inherent to the pAd5 plasmid (FIG. 8) and transformed into Ad293 cells, which leads to production of engineered viral particles according to one or more embodiment of the present invention.

In one or more embodiments, the methods of the present invention make it possible to insert a variable length DNA segment of up to about 7.5 kilo base pairs into the adenovirus serotype 5 oncolytic virus genome, which allows the introduction potentially hundreds of transcription factor binding sites per virus genome. As will be discussed in more detail below, infection of human pancreatic cancer cells with an engineered oncolytic virus according to various embodiments of the present invention containing an engineered hyper HMGA-1 binding site, each with six copies of an engineered binding site for HMGA-1, results in a reduction in cell viability after 72 hours, compared to cells without viral infection or to infection with the virus lacking the engineered hyper HMGA 1 binding site.

In addition, as set forth above, once introduced into the cancer cells, the transcription factor binding sites and/or hyper-binding sites act as decoys for binding for the targeted transcription factor so as to competitively sequester oncogenic transcription factors away from the host genomic DNA, thus abolishing or reducing oncogenic transcription factor activity, which, among other things, results in restored sensitivity to chemotherapy agents. See e.g. FIGS. 17, 18, 19, 20 and 21. The most commonly used chemotherapy agent for treating pancreatic cancer is gemcitabine. Gemcitabine is a nucleoside analog in which the 2' H atoms are replaced with fluorine of uracil. One additional nucleoside can be incorporated following gemcitabine and then DNA synthesis becomes stalled. The precise mechanism for how HMGA interferes with cancer cell sensitivity is not understood, but the empirical association has been observed.

The engineered DNA segment and general method for suppressing aberrant activity of oncogenic transcription factors of the present invention restores sensitivity of the infected cancer cells to chemotherapy agents including, but not limited to gemcitabine, erlotnib hydrochloride, irinotecan and dimethylaminopathenolide. A list of potential chemotherapy agents that can be used in combination with the engineered oncolytic viruses containing the targeted oncogenic transcription factor binding sites can be found at http://www.cancer.org/cancer/pancreaticcancer/detailedguide/pancreatic-cancer-treating-chemotherapy, and is incorporated herein by reference in its entirety. With targeting of the HMGA1 oncogenic transcription factor, the method of the present invention should be effective for any HMGA-1 positive cancer. (See FIG. 17, FIG. 18, FIG. 19, FIG. 20 and FIG. 21).

Figure 17:
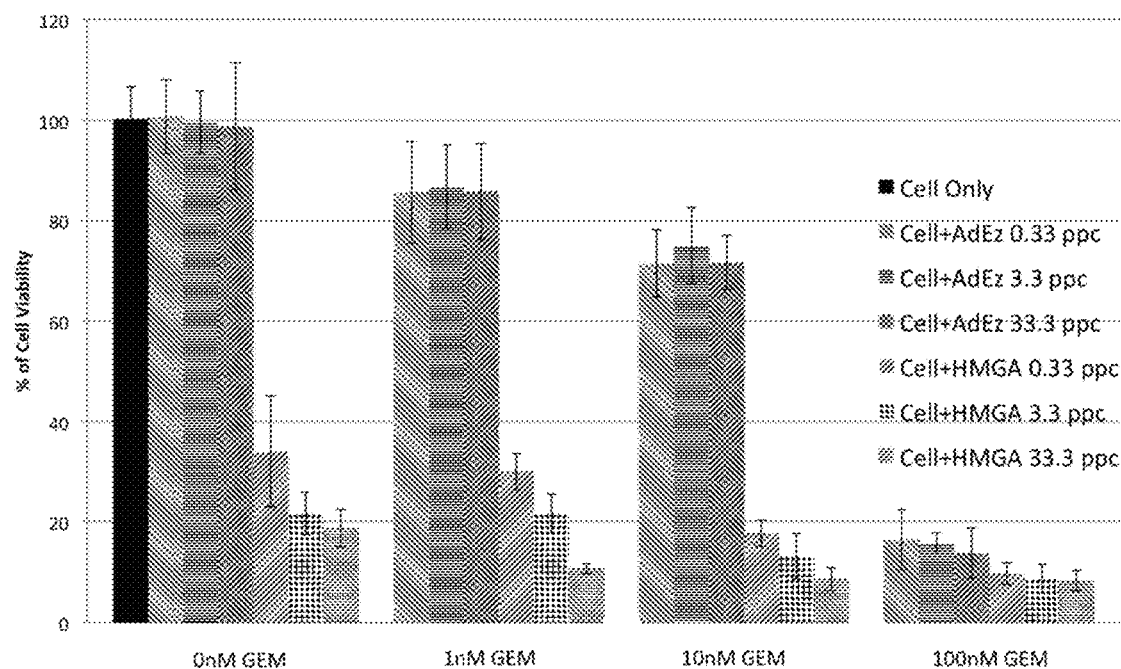
FIG. 17 is a graph comparing the effect of different concentrations of: a replication defective adeno virus (AdEz virus), AdEz virus (replication defective) carrying the HMGA-6 hyper binding site (HMGA) and Gemcitabine (GEM) on cell viability for human MiaPaCa-2 cells. $3\times10^3$ MiaPaCa-2 cells were seeded in 96 well plate 24 hour before infection. Cells were treated with different doses of either viruses with or without Gemcitabine. Cell viabilities were assessed 72 hr post treatment. Results are shown for three different GEM concentrations indicated below the graph in comparison to no GEM treatment, i.e. 0 mM GEM, and for three different viral infection concentrations, i.e. 0.33 viral particles per cell (ppc), 3.3 ppc and 33.3 ppc. All cell measurements are relative to the count of cells only shown at the far left in the 0 nM GEM group. Error bars are derived from triplicate repeated measurements.

In the embodiments shown in FIG. 17, for example, human MiaPaCa-2 pancreatic cancer cells infected with a replication defective AdEz virus carrying an engineered double stranded DNA segment having binding sites for HMGA showed a dose dependent increase in the effectiveness of Gemcitabine over a range of virus concentrations.

Figure 18:
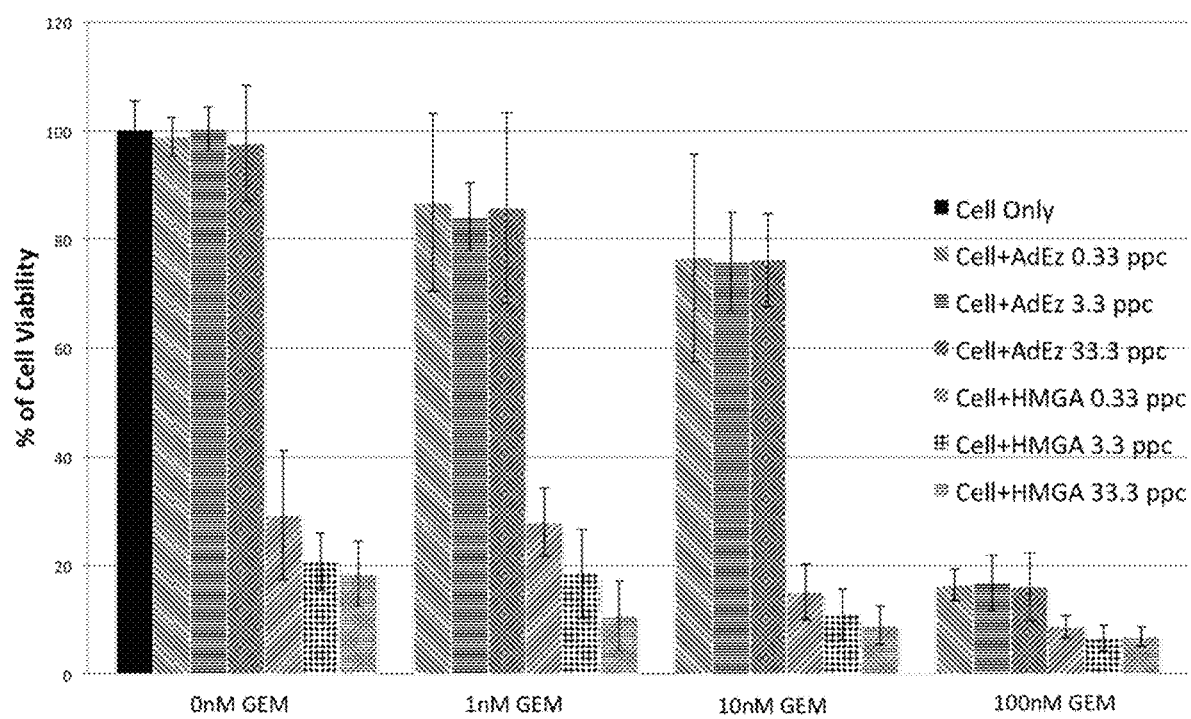
FIG. 18 is a graph comparing the effect of different concentrations of: a replication defective adeno virus (AdEz virus), AdEz virus (replication defective) carrying the HMGA-6 hyper binding site (HMGA) and Gemcitabine (GEM) on cell viability for human AsPC-1 cells. $3\times10^3$ AsPC-1 cells were seeded in 96 well plate 24 hour before infection. Cells were treated with different doses of either viruses with or without Gemcitabine. Cell viabilities were assessed 72 hr post treatment. Results are shown for three different GEM concentrations indicated below the graph in comparison to no GEM treatment, i.e. 0 mM GEM, and for three different viral infection concentrations, i.e. 0.33 viral particles per cell (ppc), 3.3 ppc and 33.3 ppc. All cell measurements are relative to the count of cells only shown at the far left in the 0 nM GEM group. Error bars are derived from triplicate repeated measurements.

In the embodiments shown in FIG. 18, for example, human AsPC-1 pancreatic cancer cells infected with a replication defective AdEz virus carrying an engineered double stranded DNA segment having binding sites for HMGA showed a dose dependent increase in the effectiveness of Gemcitabine over a range of virus concentrations.

Figure 19:
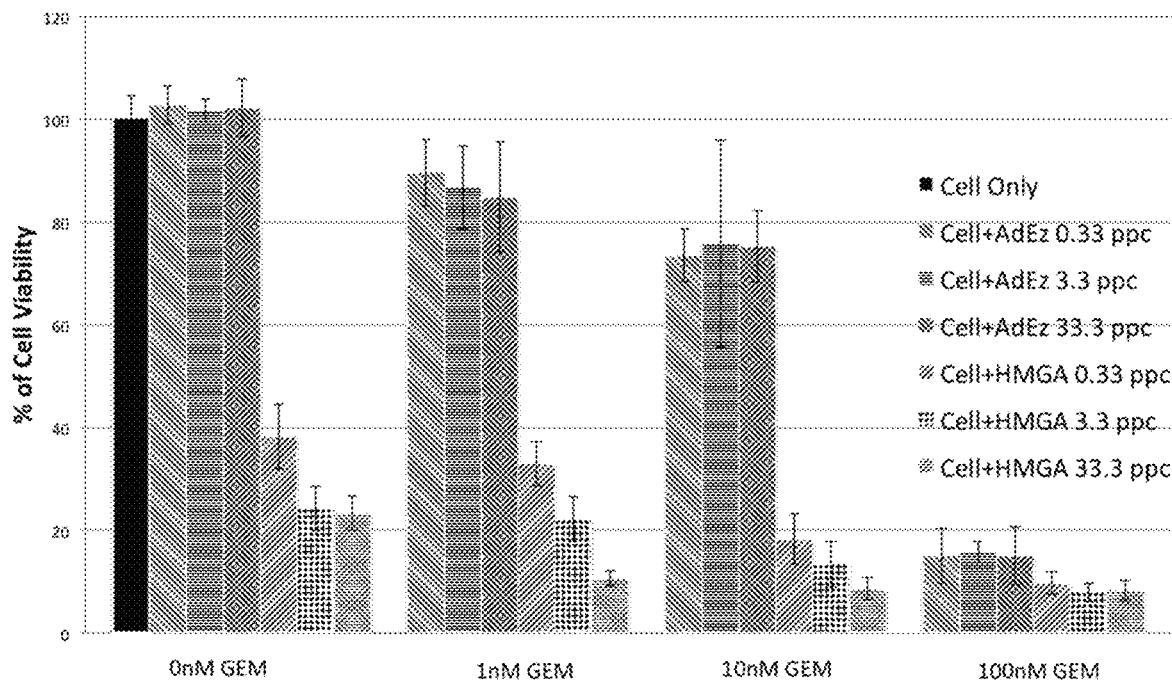
FIG. 19 is a graph comparing the effect of different concentrations of: a replication defective adeno virus (AdEz virus), AdEz virus (replication defective) carrying the HMGA-6 hyper binding site (HMGA) and Gemcitabine (GEM) on cell viability for human Panc-1 cells. $3\times10^3$ Panc-1 cells were seeded in 96 well plate 24 hour before infection. Cells were treated with different doses of either viruses with or without Gemcitabine. Cell viabilities were assessed 72 hr post treatment. Results are shown for three different GEM concentrations indicated below the graph in comparison to no GEM treatment, i.e. 0 mM GEM, and for three different viral infection concentrations, i.e. 0.33 viral particles per cell (ppc), 3.3 ppc and 33.3 ppc. All cell measurements are relative to the count of cells only shown at the far left in the 0 nM GEM group. Error bars are derived from triplicate repeated measurements.

In the embodiments shown in FIG. 19, for example, human Panc-1 pancreatic cancer cells infected with a replication defective AdEz virus carrying an engineered double stranded DNA segment having binding sites for HMGA showed a dose dependent increase in the effectiveness of Gemcitabine over a range of virus concentrations.

Figure 20:
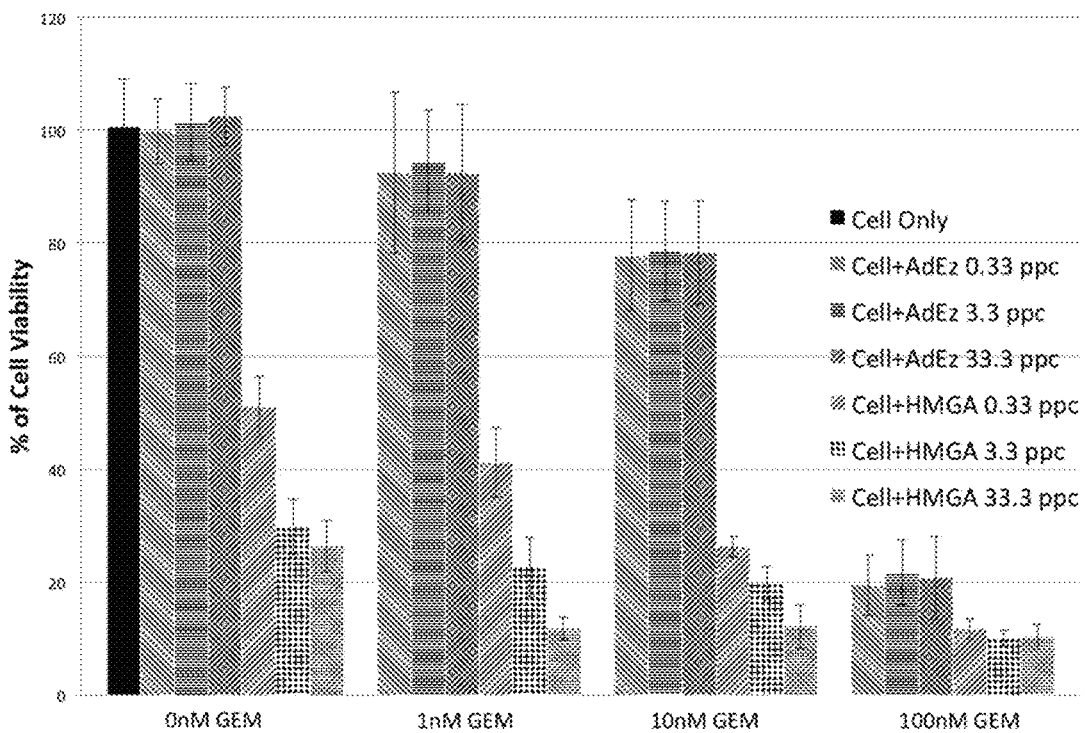
FIG. 20 is a graph comparing the effect of different concentrations of: a replication defective adeno virus (AdEz virus), AdEz virus (replication defective) carrying the HMGA-6 hyper binding site (HMGA) and Gemcitabine (GEM) on cell viability for human BxPC3 cells. $3\times10^3$ BxPC3 cells were seeded in 96 well plate 24 hour before infection. Cells were treated with different doses of either viruses with or without Gemcitabine. Cell viabilities were assessed 72 hr post treatment. Results are shown for three different GEM concentrations indicated below the graph in comparison to no GEM treatment, i.e. 0 mM GEM, and for three different viral infection concentrations, i.e. 0.33 viral particles per cell (ppc), 3.3 ppc and 33.3 ppc. All cell measurements are relative to the count of cells only shown at the far left in the 0 nM GEM group. Error bars are derived from triplicate repeated measurements.

In the embodiments shown in FIG. 20, for example, human BxPC3 pancreatic cancer cells infected with a replication defective AdEz virus carrying an engineered double stranded DNA segment having binding sites for HMGA showed a dose dependent increase in the effectiveness of Gemcitabine over a range of virus concentrations.

Figure 21:
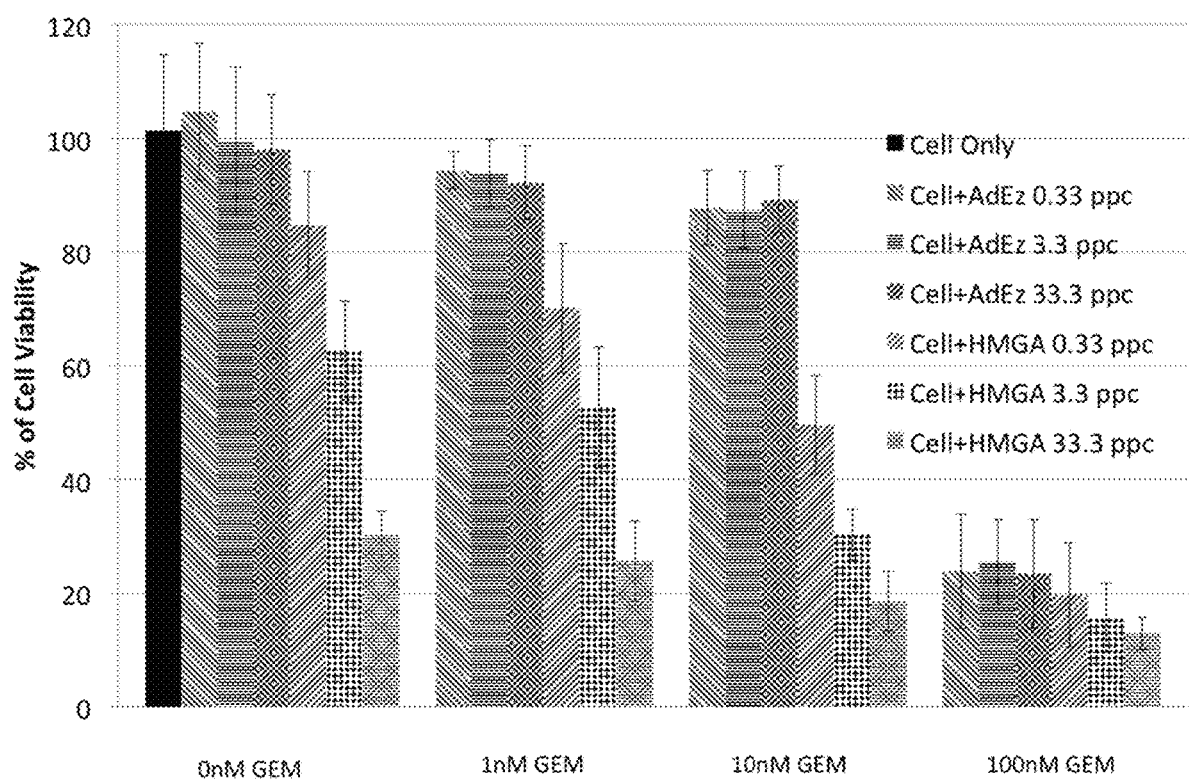
FIG. 21 is a graph comparing the effect of different concentrations of: a replication defective adeno virus (AdEz virus), AdEz virus (replication defective) carrying the HMGA-6 hyper binding site (HMGA) and Gemcitabine (GEM) on cell viability for human HepG2 cells. $3\times10^3$ Panc-1 cells were seeded in 96 well plate 24 hour before infection. Cells were treated with different doses of either viruses with or without Gemcitabine. Cell viabilities were assessed 72 hr post treatment. Results are shown for three different GEM concentrations indicated below the graph in comparison to no GEM treatment, i.e. 0 mM GEM, and for three different viral infection concentrations, i.e. 0.33 viral particles per cell (ppc), 3.3 ppc and 33.3 ppc. All cell measurements are relative to the count of cells only shown at the far left in the 0 nM GEM group. Error bars are derived from triplicate repeated measurements.

In the embodiments shown in FIG. 21, for example, human HepG2 liver cancer cells infected with a replication defective AdEz virus carrying an engineered double stranded DNA segment having binding sites for HMGA showed a dose dependent increase in the effectiveness of Gemcitabine over a range of virus concentrations.

As will be appreciated by those of skill in the art, Ad5 infection of human cells relies on binding to host cells initiated by interactions between the cellular coxsackievirus and adenovirus receptor (CAR). Although the CAR is ubiquitously expressed on human epithelial cells, it is known that CAR expression on human cancer cells is highly variable. Therefore, failure to observe an effect with certain cell lines or cancer types could be because those cells lack expression of a CAR.

Researchers have shown that a chimeric virus of adenovirus serotype 5 substituted with a subtype 3 fiber knob is capable of infecting cancer cells that lack the coxsackie adenovirus receptor, and therefore use of such chimeric adenoviruses are suitable for engineering and introduction of HMGA1 hyper binding sites as outlined here.

Experimental

To develop and further reduce the present invention to practice, DNA segments targeting the high mobility group A (HMGA) architectural transcription factor were synthesized and inserted into human cancer cells. As set forth above, HMGA overexpression is a hallmark of many human cancers. It is known that HMGA overexpression drives cancer cell proliferation and renders cancer cells resistant to chemotherapy.

A. Preparation of Replication Defective and Replication Competent Ad5 Virus Containing HMGA Hyper-Binding Sites.

HMGA is an architectural transcription factor that is highly expressed in embryonic development, not expressed or expressed at very low levels in cells of fully developed humans, and for which expression is significantly up-regulated in most cancers. HMGA overexpression in cancer cells has been associated with resistance to chemotherapy agents such as gemcitabine and with interference of p53-mediated apoptosis. As set forth above, HMGA binds AT rich DNA sequences. More specifically, it is known that that one HMGA protein binds 15-18 consecutive AT base pairs using three AT-hooks, with each AT-hook binding five to six AT base pairs. Human pancreatic cancer cells have been transfected with sulfur-substituted DNA engineered double stranded DNA segments containing a single 15-base pair HMGA binding site, partially restoring sensitivity of the cancer cells to gemicitabine. (See, Miki Watanabe, Sulaiman Sheriff, Kenneth B. Lewis, Stuart L. Tinch, Junho Cho, Ambikaipakan Balasubramaniam and Michael A. Kennedy, "HMGA1-targeted phosphorothioate DNA aptamers increase sensitivity to gemcitabine chemotherapy in human pancreatic cancer cell lines" Cancer Letters, 315, 18-27, (2012), the disclosure of which is incorporated herein by reference in its entirety). See, FIGS. 9A-B, 10A-B Here, HMGA hyper-binding sites consisting of numerous copies of the 15-base pair HMGA binding site, were inserted into the nucleus of cancer cells using an oncolytic virus delivery system. It was hypothesized that delivery of HMGA hyper-binding sites to nuclei of cancer cells would cause sequestration of overexpressed HMGA, leading to restored sensitivity to chemotherapy, restored p53-mediated apoptosis, and normalized expression of genes regulated by HMGA.

I. Design and Construction of HMGA Hyper-Binding Sites.

As set forth above, it is known that the minimum high affinity HMGA binding site consists of at least 15 consecutive A and T base pairs. It has been found that sequences containing 15 consecutive As had higher affinity compared to mixed sequences. It is believed that HMGA has higher affinity for consecutive A runs because the AT-hooks that comprise the DNA binding motifs prefer a narrow minor groove structure and the DNA minor groove reaches its narrowest possible value in DNA segments that have uninterrupted sequences of adenines. Therefore, HMGA hyper-binding sites consisting of alternating segments of 15 consecutive As and 15 consecutive Ts were constructed.

Flanking the hyper-binding sites were KpnI and HindIII restriction sites (FIG. 1), designed to enable cutting of the HMGA hyper-binding site as required for ligation into a shuttle vector in preparation for homologous recombination to insert the HMGA hyper-binding site into the vector for the replication defective Ad5, as discussed below. Also flanking the hyper-binding sites were SgrDI restriction sites engineered to allow preparation of the HMGA hyper-binding sites for insertion into the vector containing the intact Ad5ΔΔ genome.

Figure 2:
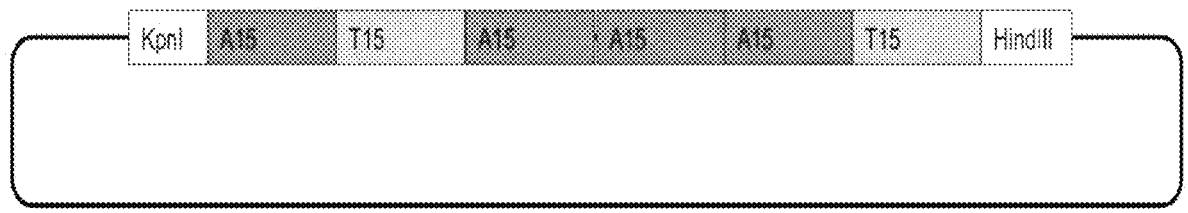
FIG. 2 is a schematic illustrating the insertion of the HMGA-6 hyper-binding site of FIG. 1 above into a shuttle vector.

The design of the initial HMGA hyper-binding site containing six tandem 15-base pair binding sites (HMGA-6) is summarized in FIG. 1. Synthetic 148 base pair linear double stranded DNA segments containing six 15-base pair binding sites and the required restriction sites were obtained commercially from Integrated DNA technologies, Coralville, Iowa. Each of the six 15-base pair binding sites contained a run of 15 consecutive As reading in either the forward or reverse direction, to ensure both segments have sufficient length to achieve the narrow minor groove structure required for tight HMGA binding.

2. Incorporation of the HMGA Hyper-Binding Sites into the Replication Defective Ad5 Virus The double stranded DNA segments containing HMGA-6 HMGA hyper-binding sites were inserted into replication defective Ad5 viruses for testing with human cancer cell lines. The resulting virus will be referred to as Ad5ΔΔ-RD-HMGA-6. The plasmid encoding the replication defective Ad5 contained most of the intact Ad5 genome, lacking only the E1 and E3 gene regions to prevent its replication (i.e. it is replication defective). Replication defective pADEasy1 plasmids in *E. coli* BJ5183 were obtained from Agilent Technologies, Inc. (Santa Clara, Calif.) (See pAdEasy-1 User Manual, (http://www.agilent.com/cs/library/usermanuals/public/240009.pdf), the disclosure of which is hereby incorporated by reference. pAdEasy-1 was chosen because it can be used in conjunction with the pShuttle-CMV system to introduce DNA elements such as the HMGA or other hyper-binding sites into the replication defective viral genome. The pShuttle-CMV plasmids used contained a multiple cloning site sandwiched between the CMV promoter and the SV40 polyadenylation signal, and as a result was suitable for insertion of large cDNA segments of up to 7.5 kb, which can be expressed in human cells under the control of the CMV promoter. Active replication of the AdEasy1 virus was accomplished by isolation of the pADEasy1 plasmid from its *E. coli* host, thereby cutting the replication defective viral genome from the plasmid, and transformation of the linearized replication defective engineered viral genome into human embryonic kidney 293 (HEK 293 or AD 293) cells engineered to contain the complementary genes deleted from the Ad5 genome required for replication. This enabled replication of the virus in the modified HEK 293 cells. In these experiments, plaques isolated from HEK 293 cells grown in standard cell growth media Dulbecco's Modified Eagle Medium (DMEM) infected with replication defective virus were grown on semisolid 4% agarose media designed for human cell growth using standard procedures.

3. Preparation of the Replication Competent Ac1.5ΔΔ Genome.

A replication competent Ad5 double mutant (Ad5ΔΔ) was created starting from the pAd5 vector containing the full intact genome. A pAd5 plasmid containing the complete Ad5 genome (See, FIG. 3) was used as the starting point. It is known that the Ad5 genome can be modified to increase specificity for replication in rapidly dividing cancer cells. This specificity was accomplished by deleting the E1ACR2 and E1B19K genes from the Ad5 genome. The E1ACR2 gene encodes a protein responsible for binding and inactivation of retinoblastoma protein (pRb), a tumor suppressor protein that prevents excessive cell growth and is dysfunctional in many cancers. The E1ACR2 protein inactivates pRb, which allows cells to proceed with growth and induces cells to move from G0 to S-phase. When E1ACR2 is deleted from the Ad5 genome, the Ad5 virus cannot replicate in cells with functioning pRb. Cancer cells often lack pRb and therefore, the Ad5 virus lacking E1ACR2 can only replicate in cancer cells and not in normal cells.

The second gene, E1B19K, encodes a protein that disrupts the tumor suppressor protein p53 pathway for apoptosis in human cells allowing replication in normal cells expressing p53. Since tumor cells are commonly deficient in p53, deletion of E1B19K in the Ad5 vector allows the Ad5 virus to replicate in cancer cells that are not expressing p53, but not in normal cells that are expressing p53. E1B19K has been shown to prevent apoptosis by death receptor and p53 pathways. Therefore, deletion of E1B19K promotes apoptosis and viral spread in cancer cells.

FIG. 4 shows an overview of the process used to engineer the Ad5ΔΔ vector, using homologous recombination to substitute DNA segments lacking each gene (carried on a shuttle plasmid) for the intact genomic sequences encoding for these genes carried in a plasmid harboring the entire Ad5 genome (FIG. 4). A more detailed schematic of the process used is shown in FIG. 5. All primers used were designed to ensure that the proper reading frame would be maintained after homologous recombination.

The Ad5ΔΔ vector was generated in two steps (FIG. 5) PCR primers AB and CD were used to amplify DNA flanking either side of the E1ACR2 gene from the pAd5 plasmid and to add a NdeI restriction site at the 5' end of the gene and a KpnI restriction site at the 3' side of the gene. As will be appreciated, the amplified "AB" per product for the upstream region of the E1ACR2 gene indicates that the forward primer was named "A" and the reverse primer was named "B". A SgrDI restriction site was introduced at the 3' end of the CD product (solid line) via the primer to enable subsequent linearization of the shuttle plasmid for the final homologous recombination step (FIG. 5). All of the AB, CD, EF, GL, and KL products were successfully generated and confirmed by sequencing. Overlapping per was used to join the AB and CD products and the product successfully incorporated into the pCU19 shuttle plasmid. Primers EF were used to amplify the E1B19K and to introduce BamHI and SaII restriction sites into the EF product (FIG. 5). These enzymes were used to cut both the shuttle plasmid carrying the ABCD product (the BamHI site is downstream of the ABCD product and the EF product, enabling joining into another shuttle plasmid. The shuttle vector was linearized using a ScaI site and the pAd5 vector using the ClaI site. Transformation of both linearized DNAs into BJ5183 led to homologous recombination, resulting in the shuttle plasmid carrying the E1ACR2 deletion mutant, pAd5ΔE1ACR2 (FIG. 4.). In this process, cells transfected with the successful homologous recombination product lose kanamycin resistance gene and retain only ampicillin resistance.

The strategy used for deleting the E1B19K gene is summarized in FIG. 6. Here, the pAd5-E1ACR2 product from FIG. 5 was linearized with the SgrDI restriction enzyme. A per product containing DNA sequence flanking, but lacking, the E1B19K gene, was generated using the GI and KL primer sets and then used for homologous recombination with the pAd5ΔE1ACR2 plasmid (FIG. 5), resulting in a plasmid containing the desired pAd5ΔΔ double deletion mutant. The pAD5 genome has a naturally occurring SpeI site between the E2 and E3 gene regions (See, FIG. 6).)

4. Incorporation of HMGA Hyper-Binding Sites into the Replication Competent Ad5ΔΔ

In these experiments, a synthetic oligonucleotide containing regions of overlap with the E2A and E3 regions separated by a SgrDI restriction site was designed and obtained by commercial DNA synthesis. As will be appreciated by those of skill in the art, the pAd5ΔΔ vector can be linearized using a naturally occurring SpeI between E2A and E3. Transformation into BJ5183 allowed homologous recombination with the commercially synthetic DNA product containing flanking regions to the SpeI site and containing the SgrDI sequence (see, FIG. 6) to enable insertion of the engineered hyper-binding sites (FIG. 8). Finally, the pAd5ΔΔ plasmid was cut and linearized from the pAd5 plasmid using the PacI restriction sites inherent to the pAd5 plasmid (see, FIG. 8) and then transformed into Ad293 cells, leading to the production of engineered viral particles that were harvested for further testing, as described below.

B. Evaluation of Ability of Replication Defective Ad5 Viruses Containing HMGA Hyper-Binding Sites to Reduce Viability, Proliferation and Chemotherapy Resistance of Human Cancer Cells.

As set forth above, the HMGA-6 hyper-binding site was successfully inserted the replication defective genome. This virus is referred to as Ad5ΔΔ-RD-HMGA-6. The Ad5ΔΔ-RD-HMGA-6 virus was used in experiments to allow measurement of the effect that the HMGA-6 hyper-binding site has on the viability, proliferation and chemotherapy resistance of human cancer cells, without the complication of the natural lytic ability of the engineered replication competent Ad5ΔΔ virus.

In these experiments, human cancer cells were infected with the replication defective Ad5 virus by adding an aliquot of suspended virus particles to a well containing the human pancreatic cancer cells.

The expected cytotoxic effect of cell replication was observed when replication defective virus was formed in AD293 cells commercially available from Agilent Technologies, Inc. (Santa Clara, Calif.) (http://www.chem-agilent-.com/pdf/strata/240085.pdf) (See, FIG. 11), which allowed viral replication because the AD293 cells are engineered to complement deleted elements missing from the double deletion mutant background. As a negative control, AD293 cells were transfected with the pUC plasmid containing the gene for green florescence protein, (pUC-GPF). As expected, no cytotoxic effect was observed (FIG. 11A) (cells uniformly adhered to the surface and no signs of detachment) since no virus was produced. In contrast, when we infected the AD293 cells with the linearized DNA encoding the native replication defective virus, i.e. with no genomic engineering, viral synthesis occurred as expected because the AD293 cells complemented the genes required for viral replication, and a cytotoxic effect (detachment and clumping of cells) was observed, indicating viral replication (FIG. 11B). Finally, when AD293 cells were transfected with linearized DNA containing the replication defective Ad5 genome containing the HMGA-6 hyper-binding site, a cytotoxic effect was observed (FIG. 11C), consistent with production of virus by the engineered Ad5-RD-HMGA-6 viral genome. Viral particle synthesis was further confirmed using immunocytofluorescence assays (FIG. 12). Cultures of AD293 cells transfected with linearized DNA encoding the native AdEz replication defective virus or the engineered Ad5-RD-HMGA-6 DNA were probed for mouse anti hexon primary antibodies and with the Alexa fluor coupled Donkey anti mouse IgG Ab with green fluorescent-tagged antibodies against the viral coat protein. Since the cells were not infected with virus, but transfected with DNA encoding the virus, positive probing for viral coat protein indicated viral synthesis inside the cells. Positive probing for viral synthesis in both, i.e. for transfection with the linearized native AdEz encoding DNA (FIG. 12A) and with the linearized Ad5-RD-HMGA-6 DNA (FIG. 12B) was observed, indicating viral syntheses in both cases.

Figure 14A:
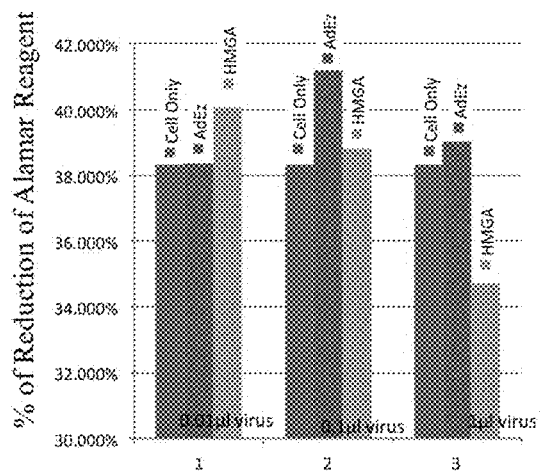
FIGS. 14A-B show the initial preliminary results of cell viability assays for MiaPaCa-2 cells.
Figure 14B:
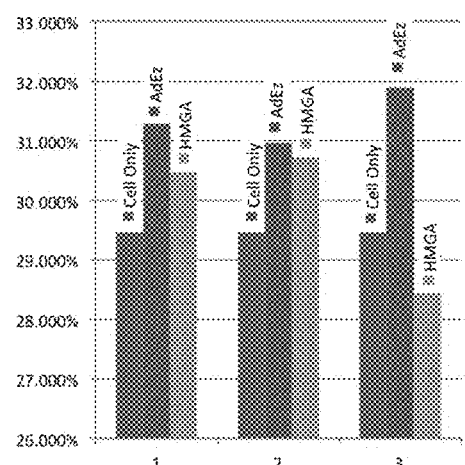

Having confirmed successful engineering of the HMGA-6 hyper-binding site into the replication defective Ad5 vector, experiments were conducted to evaluate the effect that infection with these engineered viruses has on cancer cell proliferation, cell viability, and sensitivity to chemotherapy agents. The first experiments tested the effect of infection of MiaPaCa-2 cells with replication defective Ad5 carrying the HMGA-6 hyper-binding site, i.e. Ad5ΔΔ-RD-HMGA-6 (FIG. 14). The initial results showed a promising reduction in viable MiaPaCa-2 cells 72 hours after infection compared to uninfected cells, and compared to infection with the replication defective virus lacking the HMGA hyper-binding site (FIG. 14). This result indicates that the presence of the HMGA-6 hyper-binding site on its own perturbs cancer cell proliferation or apoptosis. The results were obtained using a commercially available assay from ThermoFisher Scientific and Promega that indirectly measures the number of viable cells by monitoring production of NADH or NADPH that is carried out by live cells. The assay works by monitoring the amount of kit reagent reduced by NADH or NADPH that causes a change in the absorbance maximum of the reagent after reduction.

Figure 15A:
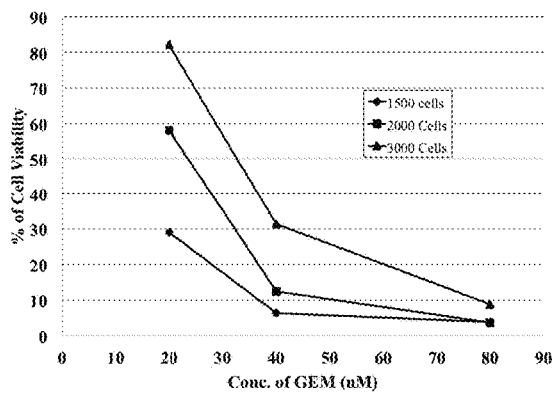
FIGS. 15A-B are graphs showing the results of MiaPaCa-2 cell viability assays in response to chemotherapy agents for gemcitabine (FIG. 15A) and irinotecan (FIG. 15B), according to one or more embodiments of the present invention. The graphs show the % remaining viable cells after 72 hours after gemcitabine (FIG. 15A) and (FIG. 15B) irinotecan treatment.
Figure 15B:
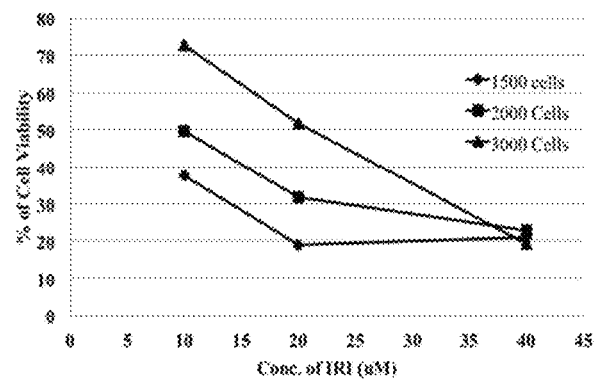

Cytotoxic effects of chemotherapy agents gemcitabine and irinotecan were also assayed. FIG. 15 shows the results of an initial assays of cell viability of MiaPaCa-2 cells as a function of dose after 72 hours of exposure. The percentage of viable cells after 72 hours is higher at low doses, however, the percentage of viable cells converges after 72 hours at higher doses.

Figure 16:
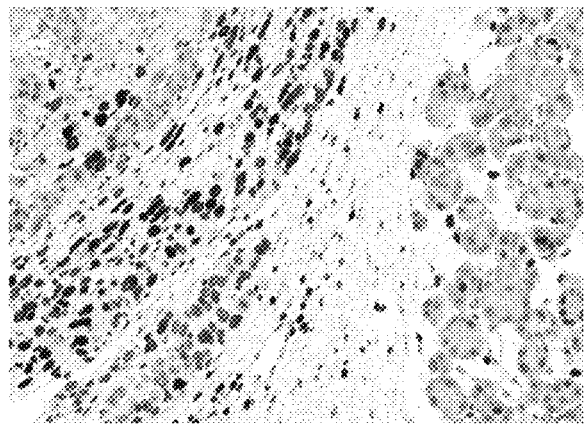
FIG. 16 is an image showing immunohistochemistry probing for HMGA expression (indicated by dark staining in the nucleus) in a section from an orthotopic pancreas tumor derived from human MiaPaCa-2 cells.

The expression of HMGA in MiaPaCa-2 cells in a tumor environment was confirmed by immunohistochemistry (FIG. 16) using an orthotopic mouse model in which MiaPaCa-2 cells were injected into the pancreas of OD.CB17-Prkdcscid/J mice, which is a type of severe combined immunodeficient (SCID) mouse that cannot generate T or B lymphocytes and is dysfunctional in cell-mediated and antibody-mediated immunity.

The effect on cell proliferation, cell viability and sensitization to chemotherapy for multiple human pancreatic cancer cell lines, and several cell lines derived from malignant tumors from several different tissue types of was evaluated for the HMGA-6 HMGA hyper-binding sites. In all human cancer cell lines tested to date, infection with replication defective engineered Ad5 viruses containing the HMGA-6 binding sites significantly reduced cell viability in comparison to cells infected with viruses lacking the HMGA-6 binding sites. In all human cancer cell lines tested to date, infection with replication defective engineered Ad5 viruses containing the HMGA-6 binding sites in combination with the chemotherapy drug gemcitabine significantly reduced cell viability in comparison to cells infected with viruses lacking the HMGA-6 binding sites in combination with the chemotherapy drug gemcitabine.

C. Evaluation of Ability of Replication Competent Ad5 Viruses Containing HMGA Hyper-Binding Sites to Reduce Viability, Proliferation and Chemotherapy Resistance of Human Cancer Cells.

The successful engineering of the replication competent Ad5ΔΔ virus was confirmed by transfecting AD293 cells with linearized Ad5ΔΔ engineered genome and observing the expected cytotoxic effect (See, FIG. 13). Viral synthesis was also confirmed by probing for the viral hexon coat protein using immunofluorescence (FIG. 13C). Preliminary tests of toxicity and distribution with the replication competent Ad5 containing HMGA hyper-binding sites are currently underway.

EXAMPLES

The following examples are offered to more fully illustrate the invention, but are not to be construed as limiting the scope thereof. Further, while some of examples may include conclusions about the way the invention may function, the inventor does not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

Human MIA PaCa2 cells, derived from a tumor of the pancreas from a 65-year old Caucasian male, were obtained from the American Type Culture Collection (ATCC) https://www.atcc.org. $3\times10^3$ MIA PaCa2 cells were seeded in a 96 well plate and grown at 37° C. for 24 hours before infection. The cells were treated/infected with a replication defective adeno virus (AdEz) viruses at different doses (0.33 particles per cell (ppc), 3.3 ppc, or 33 ppc), an AdEz virus carrying six HMGA binding sites (HMGA-6) at different doses (0.33 ppc, 3.3 ppc, or 33 ppc), or Gemcitabine (GEM) at doses of 1 nM, 10 nM, and 100 nM, with some wells being left untreated as a control. After 72 hours the post treatment cell viability for each was assessed. The results are shown in FIG. 17. At the far left in the figure in column 1, the bar indicates the number of MiaPaCa-2 cells after 72 hours when the cells are left untreated. AdEz virus (columns 2-4) does not have a significant effect on the cell viability compared to Control (column 1). In contrast, cells treated with HMGA hyper binding DNA containing virus (columns 5-7) exhibit a strong dose dependent decrease in cell viability. Columns 8-10 show the synergistic enhanced effect of combination of AdEz plus GEM in reducing cell viability at GEM concentrations of 1 nM, 10 nM, and 100 nM.

Example 2

Human AsPc-1 cells, derived from the ascites of a patient with cancer of the pancreas from a 62-year old Caucasian female, were obtained from the American Type Culture Collection (ATCC) https://www.atcc.org. $3\times10^3$ AsPc-1 cells were seeded in a 96 well plate and grown at 37° C. for 24 hours before infection. The cells were treated/infected with a replication defective adeno virus (AdEz) viruses at different doses (0.33 particles per cell (ppc), 3.3 ppc, or 33 ppc), an AdEz virus carrying six HMGA binding sites (HMGA-6) at different doses (0.33 ppc, 3.3 ppc, or 33 ppc), or Gemcitabine (GEM) at doses of 1 nM, 10 nM, and 100 nM, with some wells being left untreated as a control. After 72 hours the post treatment cell viability for each was assessed. The results are shown in FIG. 18. At the far left in the figure in column 1, the bar indicates the number of AsPC-1 cells after 72 hours when the cells are left untreated. AdEz virus (columns 2-4) does not have a significant effect on the cell viability compared to Control (column 1). In contrast, cells treated with HMGA hyper binding DNA containing virus (columns 5-7) exhibit a strong dose dependent decrease in cell viability. Columns 8-10 show the synergistic enhanced effect of combination of AdEz plus GEM in reducing cell viability at GEM concentrations of 1 nM, 10 nM, and 100 nM.

Example 3

Human PANC-1 cells, derived from the epitheloid carcinoma of a patient with cancer of the pancreas from a 56-year old Caucasian male, were obtained from the American Type Culture Collection (ATCC) https://www.atcc.org. $3\times10^3$ PANC-1 cells were seeded in a 96 well plate and grown at 37° C. for 24 hours before infection. The cells were treated/infected with a replication defective adeno virus (AdEz) viruses at different doses (0.33 particles per cell (ppc), 3.3 ppc, or 33 ppc), an AdEz virus carrying six HMGA binding sites (HMGA-6) at different doses (0.33 ppc, 3.3 ppc, or 33 ppc), or Gemcitabine (GEM) at doses of 1 nM, 10 nM, and 100 nM, with some wells being left untreated as a control. After 72 hours the post treatment cell viability for each was assessed. The results are shown in FIG. 19. At the far left in the figure in column 1, the bar indicates the number of PANC-1 cells after 72 hours when the cells are left untreated. AdEz virus (columns 2-4) does not have a significant effect on the cell viability compared to Control (column 1). In contrast, cells treated with HMGA hyper binding DNA containing virus (columns 5-7) exhibit a strong dose dependent decrease in cell viability. Columns 8-10 show the synergistic enhanced effect of combination of AdEz plus GEM in reducing cell viability at GEM concentrations of 1 nM, 10 nM, and 100 nM.

Example 4

Human BxPC-3 cells, derived from a biopsy from the body of the pancreas of a patient with cancer of the pancreas from a female, were obtained from the American Type Culture Collection (ATCC) https://www.atcc.org. $3\times10^3$ BxPC-3 cells were seeded in a 96 well plate and grown at 37° C. for 24 hours before infection. The cells were treated/infected with a replication defective adeno virus (AdEz) viruses at different doses (0.33 particles per cell (ppc), 3.3 ppc, or 33 ppc), an AdEz virus carrying six HMGA binding sites (HMGA-6) at different doses (0.33 ppc, 3.3 ppc, or 33 ppc), or Gemcitabine (GEM) at doses of 1 nM, 10 nM, and 100 nM, with some wells being left untreated as a control. After 72 hours the post treatment cell viability for each was assessed. The results are shown in FIG. 20. At the far left in the figure in column 1, the bar indicates the number of BxPC-3 cells after 72 hours when the cells are left untreated. AdEz virus (columns 2-4) does not have a significant effect on the cell viability compared to Control (column 1). In contrast, cells treated with HMGA hyper binding DNA containing virus (columns 5-7) exhibit a strong dose dependent decrease in cell viability. Columns 8-10 show the synergistic enhanced effect of combination of AdEz plus GEM in reducing cell viability at GEM concentrations of 1 nM, 10 nM, and 100 nM.

Example 5

Human HEP G2 cells, derived from a liver hepatocellular carcinoma of a 15-year-old Caucasian male, were obtained from the American Type Culture Collection (ATCC) https://www.atcc.org. $3\times10^3$ HEP G2 cells were seeded in a 96 well plate and grown at 37° C. for 24 hours before infection. The cells were treated/infected with a replication defective adeno virus (AdEz) viruses at different doses (0.33 particles per cell (ppc), 3.3 ppc, or 33 ppc), an AdEz virus carrying six HMGA binding sites (HMGA-6) at different doses (0.33 ppc, 3.3 ppc, or 33 ppc), or Gemcitabine (GEM) at doses of 1 nM, 10 nM, and 100 nM, with some wells being left untreated as a control. After 72 hours the post treatment cell viability for each was assessed. The results are shown in FIG. 21. At the far left in the figure in column 1, the bar indicates the number of HEP G2 cells after 72 hours when the cells are left untreated. AdEz virus (columns 2-4) does not have a significant effect on the cell viability compared to Control (column 1). In contrast, cells treated with HMGA hyper binding DNA containing virus (columns 5-7) exhibit a strong dose dependent decrease in cell viability. Columns 8-10 show the synergistic enhanced effect of combination of AdEz plus GEM in reducing cell viability at GEM concentrations of 1 nM, 10 nM, and 100 nM.

In light of the foregoing, it should be appreciated that the present invention significantly advances the art by providing engineered viruses containing modified viral genomes harboring artificial, non-naturally occurring hyper binding sites for targeted oncogenic transcription factors, and a general method for delivering the hyperbinding sites by using the natural infection process of the virus to deliver the hyperbinding sites directly to the nucleus of the cancer cells, thereby suppressing aberrant activity of specifically targeted oncogenic transcription factors that promote cancer progression. The engineered viruses represent a functionally improved manner of delivering double stranded DNA decoy sequences to the nucleus of cancer cells. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

The invention claimed is:

1. A method for at least one of killing and slowing the growth of cancer cells comprising High Mobility Group A (HMGA) proteins by targeting the HMGA proteins in the cancer cells, the method comprising:
   A) preparing a linear double stranded DNA segment containing one or more binding sites comprising DNA sequences that are capable of tight binding to said HMGA proteins wherein said HMGA proteins will bind to each of said one or more DNA sequences at least as tightly as it would to an HMGA consensus binding site under substantially the same binding conditions, as measured by the dissociation constant $K_d$;
   B) inserting said linear double stranded DNA segment into the genomic DNA of a double stranded DNA virus;
   C) preparing the double stranded DNA virus comprising said genomic DNA containing said linear double stranded DNA segment; and
   D) administering said double stranded DNA virus comprising the linear double stranded DNA segment directly or intratumorally into the cancer cells to infect the cancer cells and deliver the genomic DNA containing said linear double stranded DNA segment into the nucleus of said cancer cells, wherein the double stranded virus is administered to the cancer cells in an amount such that the HMGA proteins in the cancer cells bind to the one or more DNA sequences, rather than bind to the genomic DNA of the cancer cell, thereby suppressing the activity of the HMGA in the cancer cell, thereby mediating the killing or the slowing of the growth of said cancer cells.

2. The method of claim 1 wherein said one or more binding sites contains one or more copies of a consensus binding site for the HMGA proteins.

3. The method of claim 1 wherein the HMGA proteins are selected from HMG AT Hook-1 (HMGA1) proteins, High Mobility Group AT Hook-2 (HMGA2) proteins, and combinations thereof.

4. The method of claim 1 wherein said double stranded DNA virus is a replication defective adenovirus or a replication competent oncolytic adenovirus.

5. The method of claim 1 wherein said double stranded DNA virus is an adenovirus serotype 5 (Ad5).

6. The method of claim 1 wherein the step of inserting said linear double stranded DNA segment into the genomic DNA of the double stranded DNA virus (Step B) further comprises:
   a) inserting one or more restriction sites into the genomic DNA of the double stranded DNA virus;
   b) adding matching restriction sites to the ends of said linear double stranded DNA segment; and
   c) inserting said linear double stranded DNA segment into the genomic DNA of said double stranded DNA virus by homologous recombination.

7. The method of claim 1 wherein the step of inserting said linear double stranded DNA segment into the genomic DNA of a double stranded DNA virus (Step B) further comprises:
   1) preparing a plasmid containing the complete genome of Ad5;
   2) deleting the E1ACR2 and E1B19K genes from the Ad5 genome of said plasmid to create a replication competent double deletion mutant (Ad5ΔΔ) vector that promotes selective viral replication in cancer cells;
   3) preparing a synthetic oligomer comprising regions of overlap with the E2A and E3 regions of the Ad5ΔΔ vector, separated by a third restriction site;
   4) inserting the synthetic oligomer between the E2A and E3 regions of the Ad5 ΔΔ vector;
   5) amplifying said double stranded DNA sequence and incorporating it into an adenovirus shuttle plasmid; and
   6) inserting the double stranded DNA sequence into the Ad5 ΔΔ vector at the third restriction site located between the E2A and E3 regions of the Ad5ΔΔ vector.

8. The method of claim 1 wherein the step of administering further comprises co-administration of the double stranded DNA virus with a therapeutically effective amount of a chemotherapeutic agent or a pharmaceutically acceptable salt thereof.

9. The method of claim 8 further wherein said chemotherapeutic agent is selected from the group consisting of gemcitabine, erlotnib hydrochloride, irinotecan, dimethylaminopathenolide, combinations thereof, analogs thereof, and pharmaceutically acceptable salts thereof.

10. The method of claim 1 wherein said linear double stranded DNA segment has a length of from about 15 base pairs to about 7500 base pairs.

11. The method of claim 1 wherein said one or more binding sites are engineered to contain two or more copies of a consensus binding site for the HMGA proteins.

12. The method of claim 1 wherein said one or more binding sites are engineered to containing from about 1 to about 1000 copies of a consensus binding site for the HMGA proteins.

13. The method of claim 1 wherein the double stranded DNA virus of step C is administered to a patient, wherein the cancer cells are within the patient.

14. The method of claim 1 wherein said double-stranded DNA virus is selected from the group consisting of adenoviruses, vaccinia virus, Myxoma virus, herpes simplex virus 1 (HSV1), reovirus, vaccinia virus, vesiculostomatitis virus, and poliovirus.

* * * * *